United States Patent [19]

Rasmussen

[11] 4,211,867
[45] Jul. 8, 1980

[54] NITROGEN HETEROCYCLIC CARBOXIMIDAMIDE COMPOUNDS

[75] Inventor: Chris R. Rasmussen, Ambler, Pa.

[73] Assignee: McNeil Laboratories, Incorporated, Fort Washington, Pa.

[21] Appl. No.: 828,561

[22] Filed: Aug. 29, 1977

Related U.S. Application Data

[63] Continuation-in-part of Ser. No. 752,588, Dec. 20, 1976, abandoned, which is a continuation-in-part of Ser. No. 668,386, Mar. 19, 1976, abandoned.

[51] Int. Cl.² .................... A61K 31/54; C07D 417/12
[52] U.S. Cl. ................... 544/60; 260/239 A; 260/239 B; 260/239 E; 260/243.3; 260/244.4; 260/326.86; 424/246; 424/248.56; 424/250; 424/256; 424/267; 424/274; 544/129; 544/141; 544/360; 544/372; 546/186; 546/208
[58] Field of Search ............... 260/293.87, 239, 326.9, 260/239 AR, 239 E, 239 B, 243.3, 244.4, 326.86; 544/60, 111, 124, 359, 360, 141, 60, 372, 129; 546/208, 186

[56] References Cited

U.S. PATENT DOCUMENTS

| 3,903,084 | 9/1975 | DuCharme | 260/247.2 A |
|---|---|---|---|
| 3,961,065 | 6/1976 | DuCharme | 424/248 |
| 3,993,469 | 11/1976 | Regel et al. | 71/92 |
| 4,007,181 | 2/1977 | DuCharme | 260/247.5 R |

FOREIGN PATENT DOCUMENTS 1409768 10/1975 United Kingdom .

OTHER PUBLICATIONS

Burger et al, "Medincinal Chemistry", 2nd ed., (1960), p. 497.

Primary Examiner—Donald G. Daus
Assistant Examiner—Lisa Jones

[57] ABSTRACT

5-, 6- or 7-Membered fully saturated 1-azacarbocyclic-2-ylidene derivatives of guanidine having anti-secretory and hypoglycemic activities, and further useful for treatment of cardiovascular disease states.

48 Claims, No Drawings

NITROGEN HETEROCYCLIC CARBOXIMIDAMIDE COMPOUNDS

CROSS-REFERENCE TO RELATED APPLICATIONS

This application is a continuation-in-part of my copending application, Ser. No. 752,588, filed Dec. 20, 1976, which in turn is a continuation-in-part of application Ser. No. 668,386, filed Mar. 19, 1976, both now abandoned.

BACKGROUND OF THE INVENTION

In British Pat. No. 1,409,768, there are described several heterocyclic derivatives of guanidine in which the heterocyclic moiety is a 5- or 6-membered saturated 1,3-diazacarbocyclic-2-ylidene. These derivatives are unsubstituted on the imino nitrogen of the guanidine moiety. In contrast, the compounds of the present invention differ by being a saturated mono-aza heterocyclic derivative of guanidine, and, furthermore, they carry a bulky substituent on the imino nitrogen of the guanidine moiety. Additional prior art, but further related, may be represented by German Offen. No. 2,321,330 which corresponds to U.S. Pat. No. 3,993,469 and German Offen. No. 2,502,397 which corresponds to U.S. Pat. No. 3,903,084.

DESCRIPTION OF THE PREFERRED EMBODIMENTS

This invention relates to new heterocyclic derivatives of guanidine having interesting pharmacological properties and, more particularly, to such derivatives having the formula:

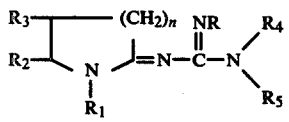

wherein:

n is the integer 1, 2 or 3;

$R_1$ is a member selected from the group consisting of hydrogen, alkyl having from 1 to 8 carbons, cycloalkyl having from 3 to 6 carbons (preferably cyclopentyl and cyclohexyl), alken-2-yl having from 3 to 5 carbons, hydroxyloweralkyl (preferably hydroxyethyl), aralkyl (preferably benzyl) and aryl (preferably phenyl);

$R_2$ is a member selected from the group consisting of hydrogen, alkyl having from 1 to 6 carbons and aryl (preferably phenyl);

$R_3$ is a member selected from the group consisting of hydrogen, alkyl having from 1 to 8 carbons and aryl (preferably phenyl);

$R_4$ is a member selected from the group consisting of hydrogen, methyl and ethyl;

$R_5$ is a member selected from the group consisting of alkyl having from 1 to 4 carbons, cycloalkyl having from 3 to 7 carbons (preferably cyclopentyl and cyclohexyl), aralkyl (preferably benzyl) and aryl (preferably phenyl and phenyl substituted with from 1 to 3 substituents each selected from the group consisting of halo, loweralkyl and loweralkoxy);

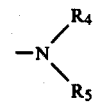

taken together represents a 3- to 7-membered saturated heterocyclic ring; provided that when —$NR_4R_5$ represents a six-membered ring, (i) said ring may, if desired, be interrupted by an oxygen or sulfur atom or by an additional nitrogen atom, which additional nitrogen atom may be substituted with loweralkyl, phenyl, or benzyl or (ii) said ring may be substituted with loweralkyl, at a carbon atom other than one immediately adjacent the nitrogen atom which is bonded to the carboximidamide function, such as, for example, aziridinyl, azetidinyl, pyrrolidinyl, piperidino, 2,3,4,5,6,7-hexahydroazepinyl, morpholino, thiamorpholino, thiamorpholino-1-oxide, thiamorpholino-1, 1-dioxide, 2, 6-diloweralkyl-morpholino (preferably 2,6-dimethyl-morpholino), 4-loweralkyl-piperazinyl (preferably 4-methyl-piperazinyl), 4-phenyl-piperazinyl, 4-benzyl-piperazinyl, 2,6-diloweralkyl-piperazinyl (preferably 2,6-dimethyl-piperazinyl) and the like; and R is a member selected from the group consisting of:
  alkyl having from 4 to 10 carbons (preferably branched), such as, for example, tert-butyl, neopentyl, 1, 1, 3,3-tetramethylbutyl and the like;
  cycloalkyl having from 5 to 8 carbons (preferably cyclopentyl and cyclohexyl);
  bicycloalkyl having from 7 to 10 carbons, such as, for example, exo-and endo-2-norbornyl, 2-bicyclo[2.2.2.]-octyl, endo-2-bicyclo[3.2.1]octyl and the like;
  bicycloalkenyl having from 7 to 10 carbons, such as, for example, anti-7-norborneyl and the like;
  tricycloalkyl having from 9 to 10 carbons, such as, for example, nor-adamantyl, 1- and 2-adamantyl, 1-and 2-(2,3,3a,4,5,6,7,7a-octahydro-4,7-methanoindanyl) and the like;
  1-adamantylmethyl;
  tricycloalkenyl having from 9 to 10 carbons, such as, for example, 3-(2,3,6,6a-tetrahydro-1H-1,3a-ethanopentalenyl),5-(3a,4,5,6,7,7a-hexahydro-4,7-methanoindenyl and the like;
  arylalkyl in which the aryl function is a member selected from the group consisting of phenyl and naphthyl and the alkyl function has from 1 to 4 carbons, such as, for example, benzyl, d- or l-α-phenethyl, α,α-dimethylbenzyl, α,α-dimethyl-β-phenethyl, d- or 1-(α-naphthyl)ethyl and the like;
  α,α-tetramethylene-phenethyl;
  diphenylalkyl in which the alkyl function has from 1 to 2 carbons, such as, for example, diphenylmethyl, 2,2-diphenylethyl and the like;
  naphthyl, including α- and β-naphthyl;
  fused diarylcycloalkenyl, such as, for example, 9-fluorenyl, 5-acenaphthyl and the like;
  fused arylcycloalkyl, such as, for example, 4-(2,3-dihydro-1H-indenyl, 1-(1,2,3,4-tetrahydronaphthyl), 7-(bicyclo[4.2.0.]octa-1,3,5-trienyl) and the like;
  phenylcycloalkyl in which the cycloalkyl function has from 5 to 7 carbons, such as, for example, cis-or trans-2-phenylcyclopentyl, cis- or trans-2-phenylcyclohexyl, cis- or trans-2-phenylcycloheptyl and the like;

cycloalkylcycloalkyl in which each cycloalkyl function has from 5 to 7 carbons, such as, for example, cis- or trans-2-cyclohexylcyclopentyl, cis- or trans-2-cyclopentylcyclopentyl and the like;

phenyl; methylenedioxyphenyl; phenyl substituted with from 1 to 3 substituents each selected from the group consisting of halo, loweralkyl and loweralkoxy; and phenyl substituted with a member selected from the group consisting of amino, dimethylamino, methylethylamino, diethylamino, loweralkanoylamino, thioloweralkyl, sulfinylloweralkyl, sulfonylloweralkyl, trifluoromethyl, hydroxy, benzyloxy, loweralkanoyloxy, loweralkanoyl and nitro;

3-Pyridyl, and 3-pyridyl substituted with from 1 to 2 substituents each selected from the group consisting of halo, loweralkyl, and loweralkoxy, such as, for example, 6-methoxy-3-pyridyl, 6-chloro-3-pyridyl, 2, 6-dimethyl-3-pyridyl, 2,6-dichloro-3-pyridyl, 2,6-dimethoxy-3-pyridyl, and the like; and 5-membered heterocyclics, such as, for example, 2-furyl and 2-thienyl.

As used herein, the prefix "lower" indicates that the relevant group has 1 to 4 carbons and the term "halo" represents halogens of atomic weight less than 127, i.e., chloro, bromo, fluoro, and iodo. Preferably, when either of the aforementioned $R_2$ or $R_3$ is alkyl or aryl, the other is hydrogen; and when n is the integer 2 or 3, then said $R_2$ and said $R_3$ is hydrogen.

Due to the presence of tertiary nitrogen in the compounds of formula (I), acid addition and quaternary salts thereof are readily obtained and such pharmaceutically acceptable salts are included within the scope of this invention. The subject compounds (I) may be converted to their therapeutically active nontoxic acid addition salt form by treatment with an appropriate acid, such as, for example, an inorganic acid, such as hydrohalic acid, e.g., hydrochloric, hydrobromic and the like, and sulfuric acid, nitric acid, phosphoric acid and the like, or an organic acid, such as, for example, acetic, propionic, glycolic, pamoic, pyruvic, malonic, succinic, maleic, fumaric, malic, tartaric, citric, benzoic, cinnamic, mandelic, methanesulfonic, ethanesulfonic, benzenesulfonic, p-toluenesulfonic, cyclohexanesulfamic, salicylic, p-aminosalicylic and the like acids. Conversely, the salt form can be converted by treatment with alkali into the free base form.

Therapeutically active quaternary ammonium salts may be prepared by reaction of the formula (I) compound with alkylating agents, i.e., alkyl, alkenyl or aralkyl halides, sulfates or sulfonate esters, such as, for example, methyl iodide, ethyl bromide, propyl bromide; allyl chloride; benzyl chloride; or di-loweralkyl sulfates-dimethylsulfate, diethylsulfate; loweralkyl arylsulfonates-methyl p-toluenesulfonate; methyl fluorosulfonate; and the like. The quaternizing reaction may be performed in the presence or absence of a solvent, depending on whether or not the quaternizing agent is itself capable of acting as the solvent also, at room temperature or under cooling, at atmospheric pressure or in a closed vessel under pressure. Suitable reaction-inert organic solvents for this purpose are ethers such as diethylether and tetrahydrofuran, hydrocarbons such as benzene and heptane, ketones such as acetone and butanone, lower alkanols such as ethanol, propanol, butanol; or organic acid amides such as formamide or dimethylformamide. The anion function of the quaternary salt is readily exchangeable by conventional ion-exchange techniques.

The most preferred compounds of this invention, in view of their exceptional hypoglycemic activity, may be illustrated by the following formula:

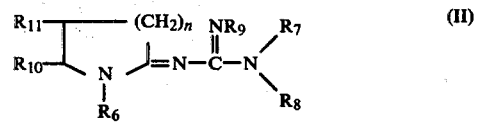

and the pharmaceutically acceptable acid additon and quaternary salts thereof wherein:

n = 1 or 2

$R_6$ is a member selected from the group consisting of loweralkyl, allyl, hydroxy-loweralkyl and benzyl;

$R_7$ is methyl or ethyl;

$R_8$ is a member selected from the group consisting of loweralkyl, cyclopentyl and cyclohexyl;

—$NR_7R_8$ taken together is a member selected from the group consisting of pyrrolidino, piperidino, morpholino and thiamorpholino;

$R_9$ is a member selected from the group consisting of phenyl, the previously described substituted phenyls, other than sulfonylloweralkylphenyl, 1-adamantyl and 1,1,3,3-tetramethylbutyl, cyclohexyl, diphenylmethyl, naphthyl and 9-fluorenyl;

$R_{10}$ is a member selected from the group consisting of hydrogen and an alkyl of 1 to 3 carbons;

$R_{11}$ is a member selected from the group consisting of hydrogen and an alkyl of 1 to 3 carbons; provided that at least one of said $R_{10}$ and $R_{11}$ is hydrogen.

The compounds of formula (I) are conveniently prepared by reacting a lactam salt of formula (III), wherein n, $R_1$, $R_2$ and $R_3$ are as previously defined, X is either methoxy or ethoxy, and $Y^\ominus$ is either $BF_4^\ominus$ or $OSO_2F^\ominus$, with a guanidine derivative of formula (IV), wherein R, $R_4$, $R_5$ and $NR_4R_5$ are as previously defined, stoichiometric quantities of reactants are preferably employed. Suitable anhydrous organic solvents for conducting the reaction include lower aliphatic alcohols, such as, for example, methanol, ethanol, 2-propanol, tert-butanol and the like; ethers, such as, for example, diethylether, tetrahydrofuran, dioxane and the like; lower halogenated hydrocarbons, such as, for example, chloroform, methylene chloride, 1,2-dichloroethane and the like; and aromatic hydrocarbons, such as, for example, benzene, toluene, xylene and the like. Ambient to 0° C. temperatures may generally be employed. The product (V), in the form of the corresponding HY salt, is converted to the corresponding base form (I) by conventional means, for example, by treatment with a suitable alkali such as alkali metal or alkaline earth metal hydroxides; carbonates and the like. The reaction may be illustrated as follows:

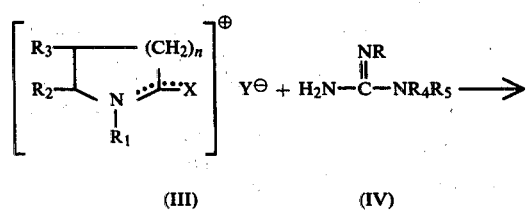

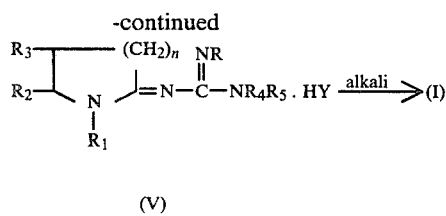

(V)

The lactam fluoborates of formula (III), wherein $Y^\ominus$ is $BF_4^\ominus$, are generally known and may be obtained according to procedures described in the literature, e.g., see Canadian Pat. Nos. 850,116 and 950,464; U.S. Pat. No. 3,876,658; Ber. 89, 2063 (1956); and Org. Synth. 46, 113, 120 (1966). The lactam fluorosulfonates of formula (III), wherein $Y^\ominus$ is $OSO_2F^\ominus$, are similarly prepared. In general, a lactam of formula (VI) is reacted with an appropriate trialkyl oxonium fluoborate (VII) or methyl fluorosulfonate (VIII) to give the corresponding lactam salt. The reaction is preferably carried out from 0° C. to ambient temperature under an inert dry atmosphere (e.g., nitrogen, argon) in an inert anhydrous lower halohydrocarbon solvent such as, for example, chloroform, 1,2-dichloroethane, methylene dichloride (most preferred) and the like. Other inert anhydrous organic solvents that may be employed include ethers such as, for example, diethyl ether, dioxane, tetrahydrofuran (THF), 1,2-dimethoxyethane and the like; and aromatic hydrocarbons such as, for example, benzene, toluene, xylene and the like. The foregoing reactions may be illustrated as follows:

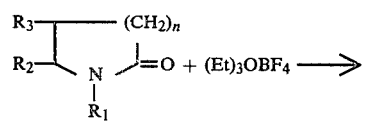

(VI) (VII)

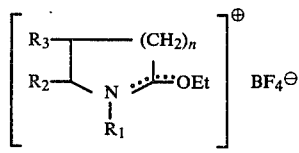

(III-a)

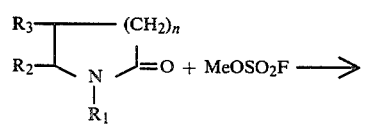

(VI) (VIII)

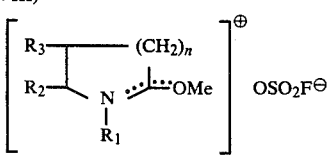

(III-b)

Alternatively, the corresponding 2-loweralkylthiolactim ethers of formula (III-c) may be prepared by reaction of the lactam of formula (VI) with $P_2S_5$ according to the procedure of R. Gompper and W. Elser, Org. Syn., Coll. Vol. V, p780–783, to yield the thiolactam of formula (VIa). Treatment of this thiolactam with loweralkylating agent such as methyliodide, methyl fluorosulfonate, dimethyl sulfate, methyl tosylate, methyl mesylate, and the like, yields the desired 2-loweralkylthiolactim ethers as the corresponding salts. Reaction of the thus-derived loweralkylthiolactim ether salts with an appropriate guanidine of formula IV yields the corresponding salts of formula I.

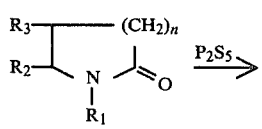

(VI)

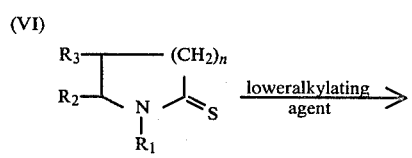

(VIa)

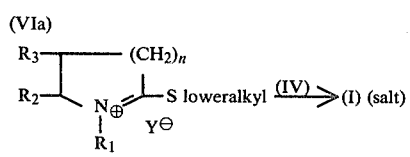

(III-c)

It has been found that, under the aforementioned conditions of reacting the formula (III-b) lactam fluorosulfonates with the formula (IV) guanidines, a side reaction may occur which gives rise to the following type of by-products:

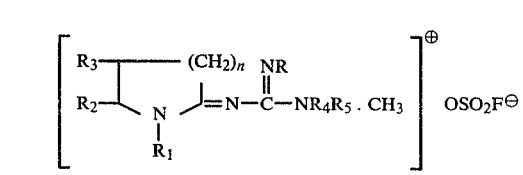

which may be isolated by conventional recovery techniques. Such salts are quaternary derivatives of formula (I) having antisecretory and hypoglycemic activity.

The preferred method of making those compounds of formula (I), when $R_1$ is hydrogen, is by reacting the free base form of (III), rather than the fluoborate or fluorosulfonate salt, with the heretofore described guanidine derivative (IV). Standard treatment of said salts of formula (III) with alkali, preferably in a halogenated hydrocarbon solvent such as methylene dichloride, chloroform and the like, readily yields the free base (IX) which is then reacted with the desired guanidine derivative (IV), preferably in an anhydrous lower alkanol solvent such as, for example, methanol, isopropanol, tert-butanol and the like, to yield the corresponding compunds of formula (I), which may exist in tautomeric form (X). Elevated temperatures up to reflux may be advantageously employed during the latter step as well as a stoichiometric excess of the free base (IX).

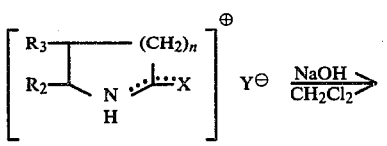

(III)

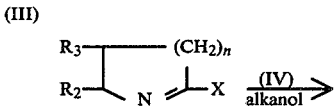

(IX)

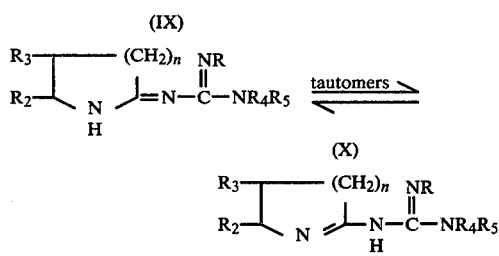

An alternative method of preparing the formula (I) compounds is by the interaction of the lactam (VI) with dimethyl sulfate (XI) to give the corresponding methosulfate salt of (III) according to the reaction conditions described by Bredereck et al., Chem. Ber. 96, 1350 (1963). The reaction is preferably carried out in an anhydrous inert organic solvent such as, for example, an aromatic hydrocarbon, e.g., benzene, toluene, xylene and the like, an ether, e.g., tetrahydrofuran, dioxane and the like, or a halocarbon, e.g., 1,2-dichloroethane, chloroform and the like. The thus-obtained methosulfate salt (XII) is then reacted with the desired guanidine derivative (IV) as before, preferably at 25° to 100° C., to yield the corresponding methylsulfate salts of formula (I), which in turn may be transformed into the corresponding free bases of formula (I) by treatment with alkali.

The free bases of formula (I) may also be obtained from methosulfate salt (XII) by reaction thereof with an alkali metal loweralkoxide, preferably sodium methoxide or sodium ethoxide in the corresponding loweralkanol solvent, according to the reaction conditions described by H. Bredereck, et al, Chem. Ber., 97, 3081–3087 (1964), to yield the corresponding lactam acetal of formula (XIIa). The lactam acetal, in turn, may be reacted with an appropriate guanidine of formula (IV) to yield the free base of formula (I). The foregoing reaction schemes may be illustrated as follows:

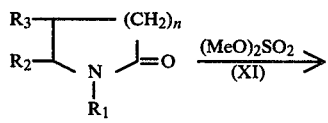

(VI)

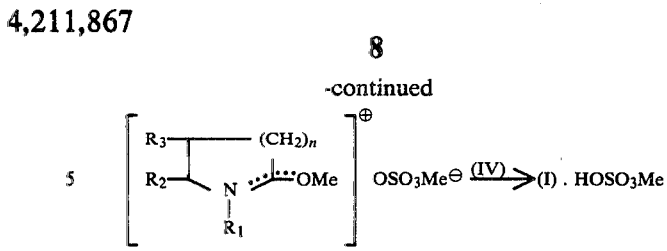

(XII)

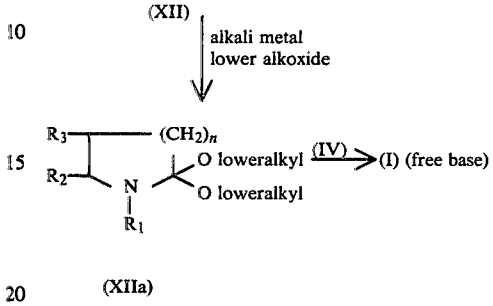

(XIIa)

Another method of preparing the formula (I) compounds is by the interaction of the guanidine precursor (IV) with a chloride salt of formula (XIII) in an anhydrous aprotic solvent, such as, for example, an ether, e.g., diethyl ether, dioxane, THF and the like, a halohydrocarbon, e.g., chloroform, methylene dichloride, 1,2-dichloroethane and the like, and, preferably, an aromatic hydrocarbon, e.g., benzene, toluene, xylene and the like. The chloride salts (XIII) are readily obtained by activation of the lactam (VI) with phosgene (ClCOCl) or thionyl chloride ($SOCl_2$) according to the directions of W. Jentzsch and M. Seefelder, Chem. Ber., 98, 274 (1965), with the evolution of $CO_2$ or $SO_2$, respectively. The foregoing reaction scheme may be illustrated as follows:

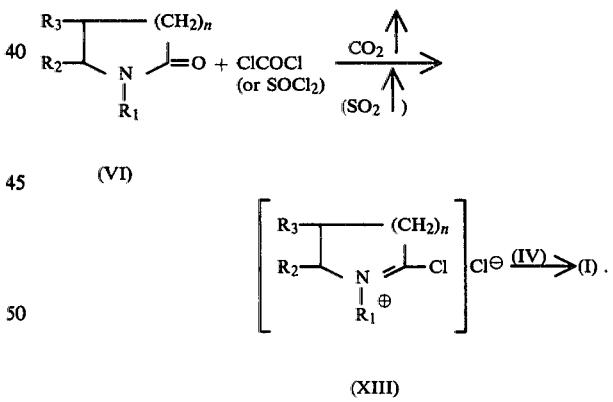

(XIII)

Instead of the aforementioned lactams (VI) starting materials, many of the subject compounds of formula (I) may also be prepared from the 2-imino compounds of formula (XIV), wherein n, $R_1$, $R_2$ and $R_3$ are as previously described. Said 2-imino compounds (XIV) are for the most part described in the literature. To the extent they are not, they may be obtained according to the methodology of Canadian Pat. N. 950,464 (e.g., see Example 14 therein). Such 2-imino precursors may be reacted with an isothiocyanate of formula (XV), wherein R is as previously described, and, preferably, other than 9-fluorenyl, in a reaction-inert organic solvent, e.g., benzene, $CH_2Cl_2$, chloroform and the like at temperatures ranging from 0° C. to ambient temperatures, for about 2 to 24 hours, in approximately equimolar amounts. The thio function (=S) in the thus-obtained thioureas (XVI), several of which are described in U.S. Pat. No. 3,717,648, is then transformed into an alkylthio function (—SR') by reacting (XVI) with an alkylating agent of the formula R'X, wherein R' is ethyl or, preferably, methyl, and X is iodide (preferably), tosylate, methosulfate, mesylate, fluorosulfonate and the like. Typical solvents for such alkylations include ethers, preferably diethyl ether, tetrahydrofuran, or dioxane, lower ketones, e.g., acetone, 2-butanone and the like; halohydrocarbons and loweralkanols, preferably methylene dichloride and methanol, respectively. Methyl iodide as the alkylating agent in methanol is particularly suitable. Generally, equimolar to a large stoichiometric excess of the alkylating agent is used, the amount depending on the reactivity of the thiourea (XVI) or its solubility in the solvent employed. The alkylation reaction may be carried out at temperatures ranging from ambient to reflux or in appropriate sealed vessels at higher temperatures. The alkylthio compounds of formula (XVII), in acid addition (HX) salt form are then reacted with an appropriate amine of the formula $HNR_4R_5$, wherein $R_4$ and $R_5$ are as previously described except for $R_5$ being phenyl or substituted phenyl, preferably in a lower alkanol solvent such as isopropanol and tert-butanol and generally at reflux temperatures, to yield the guanidine derivatives of formula (I), in similar acid addition form, which are readily obtained as the corresponding base form by conventional treatment with suitable alkali. The foregoing reactions may be illustrated as follows:

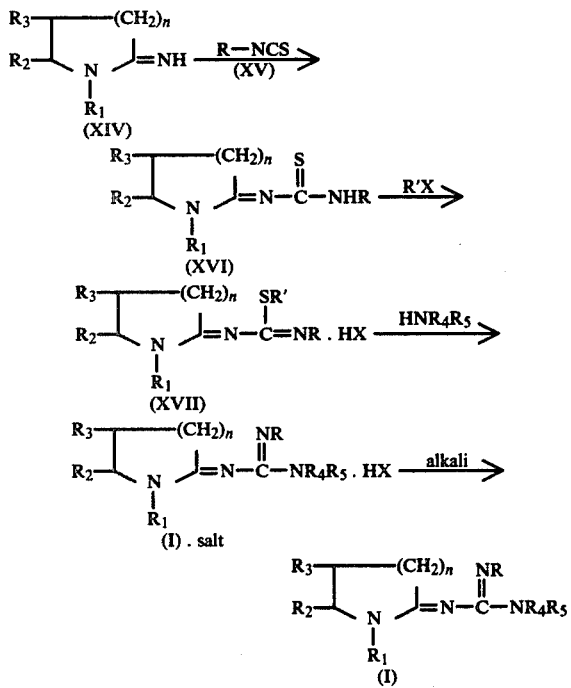

The isothiocyanates of formula (XV), many of which are known, may be prepared according to the extensive processes reported in the literature for making isothiocyanates. For example, they may be obtained from the methodologies reported by M. Bögemann et al. in "Methoden der Organische Chemie Houben-Weyl", Eugen Müller (Ed.), Georg Thieme Verlag (Publ.) Stuttgart, Germany, Vol. 9, page 867–884 (1955);

"Preparation des Isothiocyanates Aromatiques" by A. Rasschaert et al., Ind. Chim., Belge, 32, 106 (1967); German Pat. No. 1,300,559; J. Org. Chem., 36, 1549 (1971); U.S. Pat. Nos. 2,395,455 and 3,304,167; French Pat. No. 1,528,249; "A New Synthesis of Aliphatic Isothiocyanates", Angew. Chem. internat. Ed., 6, 174 (1967); Bull. Chem. Soc. Japan, 48, 2981 (1975); Tetrahedron, 29, 691 (1973); Chem. Ber., 101, 1746 (1968); and J. Indian Chem. Soc., 52, 148 (1975).

In the foregoing reaction of (XVII) with the amine, $HNR_4R_5$, it is preferred to use a stoichiometric excess of the latter, for example, in 1:1.05 to 1:2.0 molar ratios. If only a slight excess of the $HNR_4R_5$ amine is used, it may be advantageous to add a stoichiometric equivalent of a tertiary alkyl amine, e.g., $Et_3N$, in order to enhance the rate of reaction. By-products, such as:

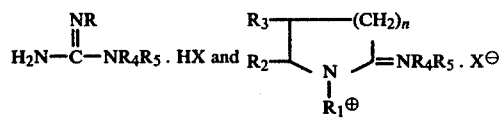

may be formed during the course of the reaction. By standard techniques known in the art, such as, for example, by fractional solubilization, such by-products can be separated from the desired formula (I) product.

Another method of preparing the formula (I) compounds from the 2-imino precursors of formula (XIV) is by the reaction of two molar equivalents of free base (XIV) with a compound of formula (XVIII), wherein $R_4$, $R_5$ and R are as previously described. During the course of the reaction, an equivalent of the 2-imino precursor in salt form (XIX) is formed. For this reason, the reaction is preferably carried out in an aprotic solvent which preferentially dissolves the desired formula (I) product in base form allowing the acid addition salt (XIX) to precipitate. The two can then be easily separated by filtration and the latter reconverted to free base by conventional treatment with alkali and made available for re-use. Typical of such preferential solvents are ethers, e.g., diethyl ether, THF and the like, lower alkanones and esters, e.g., acetone, methyl ethyl ketone, ethyl acetate and the like, aromatic hydrocarbons, e.g., benzene, toluene, xylene and the like, acetonitrile and similar solvents. Diethyl ether is generally preferred. The foregoing reaction may be illustrated as follows:

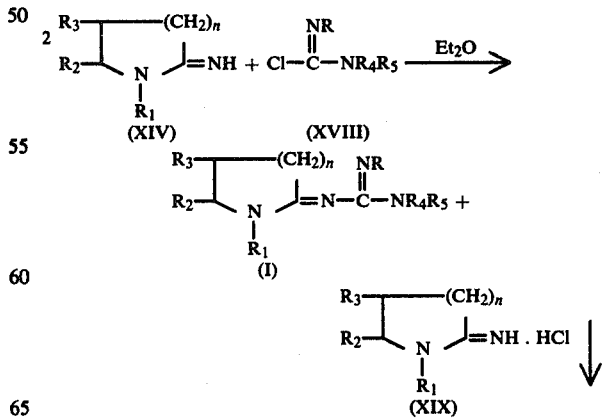

The preparation of many varied guanidine derivatives has been extensively reported on in the literature.

Accordingly, the guanidine precursors of formula (IV) are readily obtainable by several available synthetic routes. For example, a thiourea of formula (XX), wherein R is as previously described [prepared according to such methodologies as reported by R. L. Frank & P. V. Smith, Org. Syn. Coll. Vol. III, p. 735 (1955); A. Rasschaert et al., Ind. Chim. Belge, 32, 106 (1967); G. Barnikow & J. Bödeker, J. für prakt. Chemie, 313, 1148 (1971); R. G. Neville & J. J. McGee, Org. Syn. 45, 69 (1965); C. P. Joshua & K. N. Rajasekharan, Chem. & Ind. p. 750 (1974); and J. Chem. Soc. Transactions, p. 1702 (1924)], is converted to an alkylthio compound of formula (XXI) by alkylation of the former with the previously described R'X alkylating agent. The thus-obtained alkylthio compound (XXI) is then reacted with an appropriate amine of the formula $HNR_4R_5$, except where $R_5$ is phenyl or substituted phenyl, to give the guanidine derivative (XXII) in acid addition (HX) salt form which may then be converted to the corresponding base form (IV) by conventional treatment with alkali. To enhance the rate of reaction, a tertiary alkyl amine, e.g., $Et_3N$, may be advantageously employed. The reaction conditions for the foregoing are the same as those previously described for converting the thiourea (XVI) to the alkylthio compound (XVII) to the final product (I). [See. L. A. Kiselev et al., C. A., 82, 86179t (1975)].

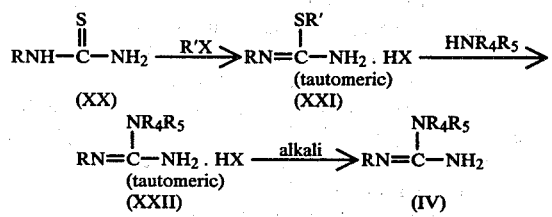

A method of preparing the guanidines of formula (IV), wherein R is phenyl or substituted phenyl, $R_4$ is hydrogen and $R_5$ is phenyl or substituted phenyl, is by starting with an appropriate N,N'diarylthiourea of formula ArNHC(=S)NHAr', wherein each of Ar and Ar' is phenyl or substituted phenyl, which is reacted with ammonia according to the method described in J. Org. Chem. (U.S.S.R.), 2 (12), 2144, (1966) (English translation)

Another method of preparing the formula (IV) guanidines, preferably wherein R is the previously described alkyl, cycloalkyl, aralkyl, diphenylalkyl, phenyl and phenyl substituted with loweralkyl, loweralkoxy, halo and nitro, is by the methodology described by E. Kühle, Angew. Chem. internat. Ed., 8, 24, 26, (1969) and references cited therein, which involves the sequential displacement of chloride from an appropriate isocyanide dihalide (XXIII). The latter, the preparation of which is described by E. Kühle et al. in Angew. Chem. internat. Ed., 6, 649 (1967), is reacted with the amine, $HNR_4R_5$, wherein $R_5$ is other than phenyl or substituted phenyl, in the presence of a trialkylamine, e.g., triethylamine, in a suitable reaction-inert aprotic anhydrous solvent such as diethyl ether, a halohydrocarbon, an aromatic hydrocarbon, and the like, to give the monohalide compound (XXIV). Treatment of the reaction mixture with excess anhydrous ammonia, followed by treatment with dilute alkali, e.g., an alkali metal hydroxide or carbonate, yields the corresponding guanidine derivative (IV).

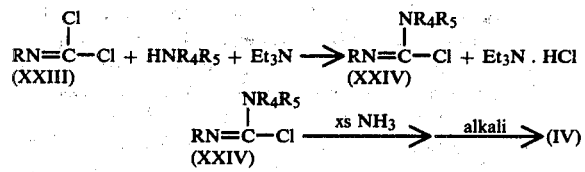

An additional method of preparing formula (IV) guanidines, wherein R is phenyl or substituted phenyl, is by reaction of an appropriate aniline (XXV) with a cyanamide of formula (XXVI) to yield the guanidine salt (XXII) according to the methodology described by N. M. Golyshin et al. in British Pat. No. 1,341,245 and Chem. Abs. 79, 66052f (1973), 80, 95571a (1974), 82, 86179t (1975) and 68, 86760g (1968).

See also J. Diamond et al., U.S. Pat. No. 3,976,643, August 24, 1976.

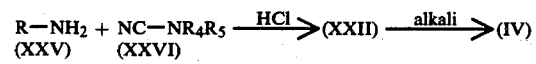

A further method of preparing formula (IV) guanidines, wherein R is phenyl or substituted phenyl, is according to the method of W. Abraham & G. Barnikow, Tetrahedron, 29, 691, 699 (1973), which describes the acidic hydrolysis of an appropriate 2-isothiocyanatoamidine of formula (XXVII), the latter being obtained from the interaction of the monohalide compound (XXIV) with ammonium thiocyanate.

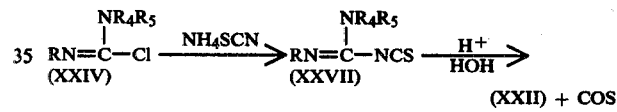

Still another method of preparing the formula (IV) guanidines, wherein R is as originally described, is according to the method of H. G. Viehe & Z. Janousek, Angew. Chem. internat. Ed., 12 (10), 806 (1973), from the interaction of an appropriate dichloromethyleneammonium salt of formula (XXVIII), except when $NR_4R_5$ is thiamorpholino-1-oxide, with an appropriate amine (XXV) to yield the corresponding monohalide compound of formula (XVIII) which is then treated with excess ammonia, followed by alkali, as before, to yield the desired guanidine derivative (IV).

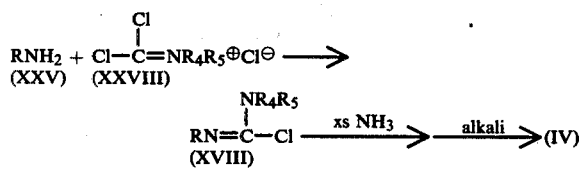

The subject compounds of formula (I) and the acid addition and quaternary salts thereof possess valuable pharmacological properties, particularly as anti-secretory and hypoglycemic agents. For example, the subject compounds of (I) and salts thereof have been found to possess anti-secretory activity by the following acute gastric fistula rat test. The anti-secretory activity of the compound to be tested is studied in female Sprague-Dawley rats after intraduodenal (i.d.) injection of the compound at doses generally ranging from 2.5–40 mg./kg. body weight. The rats are fasted 24 hours before testing and are given water ad libidum while being kept in individual cages. On the day of testing, the rats are weighed and are selected so that the rats in each test have weights within a range of ±20 g.

Surgery is carried out under light ether anesthesia. As soon as the rat is anesthetized its teeth are removed, using a small pinch pliers. A mid-line incision is made on the abdomen about 1½ cm in length and stomach and duodenum are exposed. If at this point, the stomach is filled with food or fecal material, the rat is discarded. Using 4-0 suture, a purse string stitch is placed on the fundic portion of the stomach taking care not to pierce any blood vessels in the area. A small nick is made into the stomach in the center of the purse string, and a cannula, consisting of a small vinyl tube with a flange on one end, is put into the stomach and the purse string stitch is closed tightly around the flange. Immediately following this, the test compound is administered I.D. in a volume of 0.5 ml per 100 gm rat. Three rats are generally used for each drug dose tested. Control rats receive the test vehicle, usually 0.5% aqueous methyl cellulose.

After administration of the test compound, the abdominal wall and skin are closed simultaneously with three to four 18 mm wound clips and a collecting tube is placed on the cannula. Each rat is then placed in a box in which a longitudinal slit has been made to allow the cannula to hang freely and to allow the rat to move about unencumbered. After the rat is allowed to stabilize for 30 minutes, the collection tube on the cannula is discarded and replaced with a clean tube to receive the gastric juice. Collections are made at one hour. At the end of the study, the cannula is removed at the rat is sacrificed.

The sample of gastric contents collected is drained into a centrifuge tube and centrifuged to pack down the sediment. Volumes are read and a 1 ml aliquot of the supernatant is put into a beaker containing and 10 ml distilled $H_2O$ and is titrated to pH 7 using 0.01 N NaOH. Results are determined for Volume, Titratable Acid, and Total Acid Output where Volume=total ml. of gastric juice minus sediment; Titrable Acid (milliequivalents/l)=amount of 0.01 N NaOH needed to titrate the acid to pH 7; and Total Acid Output=Titratable Acid×Volume. Results are reported in % Inhibition vs Controls and a minimum of 5% Inhibition indicates anti-secretory activity.

In addition, the subject compounds (I) and salts thereof have been found to possess blood sugar lowering activity (i.e. hypoglycemic properties) as demonstrated in the following rat glucose tolerance test, particularly those of formula (II).

The rat glucose tolerance test is a standard and extremely sensitive procedure used in the diagnosis of diabetes and hypoglycemic disease states.

In this test, male Sprague-Dawley rats (Charles River 184–250 grams) are given water ad libitum and fasted 24 hours prior to the experiment. Two to five rats are used for each test and control group. Test Compounds, 1–200 mg./kg., are administered (s.c., i.p. or orally) suspended in 0.5 or 1.0 milliliter, but preferably the former, of 0.5–1.0% methylcellulose vehicle. Control animals are given an equal amount of vehicle. Serial blood samples (0.1 milliliter) are obtained from the tail without anesthesia prior to and at 30, 60, 90, 120, 150 and 180 minutes after administration of 0.8 to 1.0 gram of glucose per kilogram of body weight in 1 milliliter of water. (The glucose is given orally if the test compound has been given parenterally, and subcutaneously if the test compound has been given orally.) Specimens of blood are immediately deproteinized with aqueous solutions of $Ba(OH)_2$ and $ZnSO_4$ and glucose levels are determined using the glucose oxidase assay described by L. P. Cawley et al., "Ultra Micro Chemical Analysis of Blood Glucose with Glucose Oxidase", Amer. J. Clin. Path., 32, 195 (1959). The blood glucose values at each time point are expressed in terms of milligram percent (mg glucose/100 ml of blood). The mean glucose values of the controls are compared statistically by the Student's t-Test to the means of the experimental group at each of the corresponding time points. If the compound lowers the blood glucose significantly at any time at a 95% confidence limit, the compound is considered to have hypoglycemic activity. The blood glucose lowering, expressed as percent lowering, is obtained by dividing the difference between the mean blood glucose values for test and control animals by the mean glucose value for the control animal.

In addition, the compounds of this invention have been found to be useful agents for the treatment of cardiovascular disease states such as angina pectoris, and atrial and/or ventricular arrhythmias by virtue of their activity in experimental laboratory animals at total doses of 1.0–17.5 mg/kg i.v. in one or more of the following tests.

Test A. Hemodynamic evaluation (determination of acute effect on arterial pressure, heart rate and electrocardiogram, and of interaction upon autonomic reflexes). To mongrel dogs (previously anesthetized using thiopental sodium, 20 milligrams per kilogram i.v. for induction and alpha-chloralose, 60 milligrams per kilogram i.v. for maintenance), a cuffed endotracheal tube is inserted to maintain a patent airway and the animals are allowed to breath spontaneously. A femoral artery and vein are isolated and catheterized for recording of arterial pressure and intravenous injection, respectively. Both common carotid arteries are isolated for performance of bilateral carotid occlusion. The right vagus nerve is stimulated electrically for ten seconds at 5 volts, 20 pulses per second of 2 millisecond duration to obtain cardiac arrest. The electrocardiogram is monitored through Limb Lead II. Two control responses are obtained to the following pharmacological procedures: epinephrine, 4 mcg/kg i.v.; bilateral carotid occlusion, 30 sec.; dimethylphenylpiperazinium (DMPP), 10 mcg/kg i.v.; peripheral vagal stimulation, 10 sec.; acetylcholine, 10 mcg/kg i.v.; angiotensin, 1 mcg/kg i.v. Test Compounds are evaluated at a dose of 10 mg/kg i.v. employing bolus injections over approximately a one minute period. The effect of the test compound is noted on the electrocardiogram, arterial pressure and heart rate. Ten minutes after administration of compound, another series of hemodynamic responses is obtained. The intraveneous administration of DMPP stimulates autonomic ganglion resulting in an inhomogeniety within the cardiac conduction system resulting in arrhythmias. Agents possessing anti-arrhythmic activity prevents these arrhythmias subsequent to DMPP administration.

Test B. Reflexogenic Sinus Tachycardia (Cardiac-slowing): A bilateral vagotomy is performed on the anesthetized dog [anesthesia consists of i.v. administration of thiopental sodium (20 mg/kg) maintained by subsequent i.v. injections of $\alpha$-chloralose (60 mg/kg)]. Two doses of aminophylline (5 mg/kg i.v.) are administered at 15-minute intervals. The hypotensive effect of aminophylline activates the baro-receptors of the carotid sinus which, in turn, stimulates the sympathetic nervous system causing a reflux rise in the heart rate. Fifteen minutes after the second dose of aminophylline, the compound to be tested is administered i.v. and the effect on the heart rate is noted over a 30-minute period. Compounds showing heart-rate lowering activity of at least 18 sinus beats per minute for at least 5 minutes are considered to be active. Such compounds are useful in the treatment of angina pectoris since heart rate is considered to be a major determinant of myocardial oxygen consumption.

Test C. Ventricular Anti-arrhythmic Activity is evaluated by either of the following two tests.

Test C-1. Mongrel dogs are anesthetized with pentobarbital sodium (30 mg/kg) i.v. A left-sided thoracotomy is performed and the left anterior descending coronary artery is ligated according to the procedure of S. A. Harris, Circ. 1, 1318 (1950). Eighteen to twenty-four hours later, the animal recovers from the anesthesia and a full blown multifocal ventricular tachycardia develops. The test compound is then administered i.v. and the effect on the arrhythmia is noted. The degree of protection is determined by expressing the ratio of normal sinus beats to heart rate as a percentage. At least a 25% reversion to normal sinus rhythm lasting at least 15 minutes indicates positive ventricular anti-arrhythmic activity.

Test C-2. A cuabain-induced ventricular antiarrhythic test: Limb lead II of the electrocardiogram and arterial blood pressure recordings on the anesthetized dog (anesthesia same as in Test B) are first obtained. Ouabain (70 mcg/kg i.v.) is given and readministered at 15-minute intervals in 10 mcg/kg increments until a ventricular tachycardia is sustained for 10 minutes. The test compound is then administered i.v. Effectiveness is assessed by the ability of the drug to revert the tachycardia to normal sinus rhythm.

Test b. Atrial Anti-arrhythmic Test: The right atrium of an anesthetized dog (anesthesia same as in Test B) is exposed by right thoracotomy and retraction of the pericardium. Atrial fibrillation, as determined by standard ECG limb lead (II), is induced by placing two drops of a 10% solution of acetylcholine on the atrium and then stroking the atrium with a blunt spatula. The period of fibrillation is recorded. Two control periods of fibrillation are produced at 15-minute intervals. The compound to be tested is administered i.v. ten seconds after the next induction. A compound is classified as active if it decreases the period of fibrillation by at least 50%. The minimum dose which causes such 50% decrease is called the minimum effective dose (MED).

In the following table, the activity of several of the subject compounds is listed, as demonstrated by their relative positive responses to one or more of the aforementioned at a total dose of 1.0-17.5 mg/kg i.v. It is understood that the compounds listed therein are not stated for purposes of limiting the invention thereto, but only to show the useful properties of all the compounds within the scope of formula (I) in base or salt form.

| Compound of Example No. | Active in Test(s) | Compound of Example No. | Active in Test(s) |
| --- | --- | --- | --- |
| ID, XIV | A, C-1, C-2, D | XV 11 | A |
| VI 1 | D | XV 13 | A, B |
| VI 4 | D | XV 14 | A |
| VI 5 | A | XV 15 | C-2, D |
| VI 7 | B | XV 16 | A |

-continued

| Compound of Example No. | Active in Test(s) | Compound of Example No. | Active in Test(s) |
| --- | --- | --- | --- |
| VI 11 | A | XV 21 | A, D |
| VI 14 | A | XV 22 | A |
| VI 16 | A | XV 23 | A |
| VI 19 | A | XV 26 | A, B |
| VI 22 | A | XV 27 | A |
| VI 23 | A | XV 31 | A |
| XV 3 | A | XVI | A |
| XV 5 | A | XVII 1 | D |
| XV 6 | A | XVIII 2 | A |
| XV 7 | C-2, D | XVIII 3 | A, D |
| XV 8 | A | | |

The subject compounds (I), in base or acid addition salt form, may be formulated into conventional pharmaceutical dosage forms and preparations, for example, for oral and parenteral administration, according to standard pharmaceutical techniques in the art.

EXAMPLE I

A.
N-(1-Methyl-2-pyrrolidinylidene)-N'-phenylthiourea:

To 6.73 g (0.05 mole) of 2-imino-1-methyl-pyrrolidine hydrochloride, as a stirring suspension in benzene, is added 5 ml of 50% aqueous NaOH solution. After stirring about 2 minutes, the organic layer is decanted onto $K_2CO_3$ (anhyd.) and the extraction is repeated twice with fresh benzene. The combined extracts, after drying, are quickly filtered (diatomaceous earth pad) with suction, minimizing air contact to avoid carbonate salt formation, and 6.76 g (0.05 mole) of phenylisothiocyanate is added in one portion. After stirring for three hours, the resulting solid is collected. A second crop is obtained from the mother liquor. Recrystallization from ethyl acetate gives pure product; N-(1-methyl-2-pyrrolidinylidene)-N'-phenylthiourea, m.p. 142°–143.5° C.

B. Methyl N-(1-methyl-2-pyrrolidinylidene)-N'-phenylcarbamimidothioate Hydroiodide:

To a solution of 34.86 g (0.15 mole) of N-(1-methyl-2-pyrrolidinylidene)-N'-phenylthiourea in 500 ml of acetone is added 21.3 g (0.15 mole) of iodomethane in acetone. The solution is refluxed for ½ hour and allowed to stand at room temperature for an additional hour. A solid, crystallizes upon cooling (ice bath). Following recrystallization from methanol-isopropanol, pure methyl N-(1-methyl-2-pyrrolidinylidene)-N'-phenylcarbamimidothioate hydroiodide is obtained; m.p. 145°–147° C.

C. Treatment of the compound of Example I-A in either lower alkanol solvents, acetone, or lower halohydrocarbons with either methyl p-toluenesulfonate, dimethyl sulfate, methyl fluorosulfonate, trimethyloxonium fluoborate or methyl methanesulfonate affords the methylthio compound of Example I-B as the corresponding respective salt.

D.
N-(1-Methyl-2-pyrrolidinylidene)-N'-phenyl-1-pyrrolidinecarboximidamide Hydroiodide:

A solution of 15.02 g (0.04 mole) of the compound of Example I-B and 4.31 g (0.06 mole) of 99% pyrrolidine in 100 ml of isopropanol is refluxed for twenty-four hours. A solid crystallizes upon cooling (ice). The crystals are collection by filtration and the mother liquor set aside (see Example XXVI). After recrystallization of the crystals from isopropanol and methanol-ether, pure N-(1-methyl-2-pyrrolidinylidene)-N'-phenyl-1-pyrrolidinecarboximidamide hydroiodide is obtained; m.p. 206°–208° C.

EXAMPLE II

In accordance with Canadian Pat. No. 950,464, there are obtained the following acid addition salts of the 2-imino compounds of formula (XIV):
 a. 2-imino-1-methyl-5-phenylpyrrolidine fluoborate, m.p. 128°–31° C.;
 b. 2-imino-1-methyl-pyrrolidine fluoborate, m.p. 109°–11° C.;
 c. 2-imino-1-ethyl-pyrrolidine hydrochloride, m.p. 181°–85° C.;
 d. 2-imino-1-n-butyl-pyrrolidine cyclohexanesulfamate, m.p. 110°–114.5° C.;
 e. 2-imino-1-benzyl-pyrrolidine fluoborate, m.p. 112–114° C.;
 f. 2-imino-1,5-dimethyl-pyrrolidine fluoborate, m.p. 100°–102° C.;
 g. 2-imino-1-methyl-piperidine hydrochloride; and
 h. hexahydro-2-imino-1-methyl-1H-azepine cyclohexanesulfamate, m.p. 143°–45° C.
 i. 1-hydroxyethyl-2-iminopyrrolidine cyclohexanesulfamate, m.p. 105°–108° C.

Each of the foregoing salts is converted to the free base form by treatment with 50% NaOH as shown in Example I-A.

EXAMPLE III

By following the procedure described by J. C. Jochims & A. Seeliger, Angew. Chem. internat. Ed., 6 (2), 174 (1967) for making isothiocyanates, the following are obtained:
 a. 1- and 2-(2,3,3a,4,5,6,7,7a-octahydro-4,7-methanoindanyl)isothiocyanates;
 b. 1,1-Dimethylphenethyl isothiocyanate;
 c. 1-α-Phenethyl isothiocyanate;
 d. d-α-Phenethyl isothiocyanate;
 e. 1-Benzylcyclopentyl isothiocyanate;
 f. 7-(Bicyclo[4.2.0]octa-1,3,5-trienyl)isothiocyanate;
 g. 1-Adamantylmethyl isothiocyanate;
 h. 2-Adamantyl isothiocyanate;
 i. trans-2-Phenylcyclopentyl isothiocyanate;
 j. cis-2-Phenylcyclopentyl isothiocyanate;
 k. trans-2-Cyclohexylcyclopentyl isothiocyanate;
 l. cis-2-Cyclohexylcyclopentyl isothiocyanate; and
 m. cis-2-Phenylcycloheptyl isothiocyanate.

EXAMPLE IV

By following the procedure of Example I-A, except that an equivalent amount of an appropriate 2-imino compound obtained from Example II is used as starting material in reaction with an equivalent amount of an appropriate isothiocyanate there are obtained, as respective products, the following thioureas of formula (XVI):
 a. N-2-(hexahydro-1H-1-methyl-azapinylidene-N'-phenylthiourea, m.p. 157°–59° C.;
 b. N-1-methyl-2-pyrrolidinylidene-N'-diphenylmethylthiourea, m.p. 112°–114° C. (polymorph), 119°–120° C.;
 c. N-1-methyl-2-pyrrolidinylidene-N'-p-nitrophenylthiourea, m.p. 179°–180.5° C. (dec.);
 d. N-1-methyl-5-phenyl-2-pyrrolidinylidene-N'-phenylthiourea, m.p. 135°–140° C.;
 e. N-1-methyl-2-pyrrolidinylidene-N'-p-fluorophenylthiourea, m.p. 152°–54° C.;
 f. N-1-methyl-2-pyrrolidinylidene-N'-benzylthiourea m.p. (71) 74°–81° C.;
 g. N-1-methyl-2-pyrrolidinylidene-N'-2-naphthylthiourea m.p. 159°–162° C. (dec.);
 h. N-1-methyl-2-pyrrolidinylidene-N'-cyclohexylthiourea m.p. 88°–93° C.;
 i. N-1-methyl-2-pyrrolidinylidene-N'-p-methoxyphenylthiourea, m.p. (149) 150°–152° C. (dec.);
 j. N-1-methyl-2-pyrrolidinylidene-N'-p-chlorophenylthiourea, m.p. 154°–156.5° C. (dec.);
 k. N-1-methyl-2-pyrrolidinylidene-N'-2,6-dimethylphenylthiourea, m.p. (164) 165°–68° C.;
 l. N-1-methyl-2-pyrrolidinylidene-N'-1,1,3,3-tetramethylbutylthiourea; m.p. 115°–116.5° C.;
 m. N-1-methyl-2-pyrrolidinylidene-N'-1-adamantylthiourea, m.p. 150°–52° C.;
 n. N-1-ethyl-2-pyrrolidinylidene-N'-phenylthiourea, m.p. 158° C.;
 o. N-1-ethyl-2-pyrrolidinylidene-N'-p-methoxyphenylthiourea, m.p. 128°–30° C.; and
 p. N-1-methyl-2-piperidinylidene-N'-phenylthiourea, m.p. 132°–34° C.

EXAMPLE V

The S-methylation procedure of Example I-B is followed, utilizing the indicated solvent with the thiourea precursor of Example IV as the starting material to be methylated, to yield the following methylthio hydroiodide salts of formula (XVII):

| Example IV Precursor | Solvent | S-Me . HI (m.p.) |
| --- | --- | --- |
| a | CH$_2$Cl$_2$ | 157°–59° C. |
| b | acetone | 122°–23° C. |
| c | MeOH | — |
| d | MeOH | 150°–52° C. |
| e | MeOH/acetone | 104°–105° C. |
| f | acetone | 123°–25° C. |
| g | CH$_2$Cl$_2$ | glass |
| h | CH$_2$Cl$_2$ | (oil) |
| i | CH$_2$Cl$_2$ | 124°–25° C. |
| j | CH$_2$Cl$_2$ | 165°–68° C. |
| k | CH$_2$Cl$_2$ | 189°–92° C. (dec.) |
| l | MeOH | (oil) |
| m | MeOH | 145°–48° C. |
| n | CH$_2$Cl$_2$ | 117°–19° C. |
| o | acetone | (oil) |
| p | acetone | 164°–65° C. |

EXAMPLE VI

The procedure of Example I-D is followed in preparing the guanidine derivatives of formula (I) as the free base or acid addition salt, except that an appropriate methylthio hydroiodide precursor obtained from Examples I-B and V and an appropriate amine of the formula HNR$_4$R$_5$ are used as starting materials in a 1:1.5 to 1:3 molar ratio, respectively, in refluxing isopropanol or, preferably, tert-butanol to yield the respective formula (I) product as the corresponding hydroiodide salt, which is then isolated as such, or converted to the corresponding base form by conventional treatment with aqueous alkali, or reconverted to another acid addition salt by reaction of the base form with the indicated acid. In addition, the formula (IV) guanidines may be formed as by-products and may be isolated from the reaction mixture, e.g., by selective solubilization or fractional crystallization techniques, either as the free base or acid addition salt form.

a. N-benzoyl-N'-3,4-dimethoxyphenylthiourea, m.p. 133°-34° C.;

| Compound | S-Me . HI Precursor | —NR₄R₅ | Formula (I) Product Form | m.p. (°C.) |
|---|---|---|---|---|
| 1 | Example I-B | —N(piperidine) | HI | 198–200 |
| 2 | Example I-B | —NH-cyclopentyl | HI | 186–188.5 |
| 3 | Example I-B | —N(N-Ph piperazine) | base | 131–33 |
| 4 | Example I-B | —N(morpholine) | HI | (163–4) 171–73 |
| 5 | Example I-B | —NH-cycloheptyl | base | 82–84 |
| 6 | Example I-B | —N(Me)CH₂Ph | HI | 180–82 |
| 7 | Example I-B | —N(N-Me piperazine) | HI | 161–161.5 |
| 8 | Example I-B | —N(2,6-dimethylmorpholine) | HI | (193) 197–199 dec |
| 9 | Example I-B | —N(2,6-dimethylpiperazine) | 2 HI | 269–270 dec |
| 10 | Example V-a | —N(pyrrolidine) | HI | 192–93 |
| 11 | Example V-b | " | " | 218–20 |
| 12 | Example V-d | " | " | 201–03 |
| 13 | Example V-e | " | " | 190–92 |
| 14 | Example V-f | " | " | (165) 167–71 |
| 15 | Example V-g | " | " | 187–89 |
| 16 | Example V-h | " | " | 203–04 |
| 17 | Example V-i | " | " | 142–44 |
| 18 | Example V-j | " | " | 183–85 |
| 19 | Example V-l | " | HClO₄ | 154–55 |
| 20 | Example V-m | " | HI | 171–73 |
| 21 | Example V-n | " | " | 142–43 |
| 22 | Example V-o | " | " | 164–66 |
| 23 | Example V-p | " | " | 151–53 |

EXAMPLE VII

A. This example illustrates the preparation of N-benzoyl thioureas according to the methods of R. L. Frank & P. V. Smith, Org. Synth. Coll. Vol. III, p. 735 (1955) [See Also G. Barnikow & J. B. Bodeker, J. prakt. Chemie, 313, 1148 (1971)]. Accordingly, the following benzolthioureas are prepared:

b. N-benzoyl-N'-p-benzoyloxyphenylthiourea, m.p. (120) 132°-37° C.
c. N-benzoyl-N'-(4-methylthiophenyl) thiourea, m.p. 160°-161° C.

B. Substituting carbethoxyisothiocyanate for benzoyl isothiocyanate one obtains N-carbethoxy-N'-(3,4-methylenedioxyphenyl) thiourea, m.p. (137) 146°-148° C.

EXAMPLE VIII

This example illustrates the hydrolysis of appropriate benzoylthioureas and carbethoxythioureas to the thioureas of formula (XX) according to the methodology described by R. L. Frank & P. V. Smith, Org. Syn. Coll. Vol. III, p. 735 (1955).

A. 3,4-Dimethoxyphenylthiourea. To a one liter beaker containing 95.85 g. (0.302 mol) of N-benzoyl-N'-3,4-dimethoxyphenylthiourea is added 230 ml of 10-12% NaOH solution and 60 ml of $H_2O$. The mixture is heated to temperatures of about 60°-80° for 5-10 mins. until hydrolysis is completed. Filtration of the hot solid, followed by washing with water until the filtrate becomes neutral, then washing with MeOH and drying gives the product, 3,4-dimethoxyphenylthiourea; m.p. 234°-242° C. (dec.).

B. p-Benzyloxyphenylthiourea: The foregoing procedure of Example VIII-A is repeated, except that an equivalent amount of N-benzoyl-N'-p-benzyloxyphenylthiourea is used as the material to be hydrolyzed, to yield p-benzyloxyphenythiourea as the product, m.p. 193°-95° C.

C. 4-Methylthiophenylthiourea, m.p. (187) 190°-191° C., is similarly obtained.

D. 3,4-Methylenedioxyphenylthiourea, m.p. 207°-209° C., Alkaline hydrolysis of N-carbethoxy-N'-(3,4-methylenedioxyphenyl) thiourea under conditions described above followed by neutralization with mineral acid (Caution: vigorous $CO_2$ evolution) affords 3,4-methylenedioxyphenylthiourea, m.p. 207°-209° C.

EXAMPLE IX

This example illustrates the preparation of formula (XX) thioureas according to the method of C. P. Joshua & K. N. Rajasekharan, Chem. & Ind., p. 750 (1974).

A. 4-n-Butylphenylthiourea: To 100 ml of hot HCl (18%) is added 90.2 g (0.605 mole) of p-n-butylaniline (97%) followed by 46.1 g (0.605 mole) of $NH_4SCN$. The resultant mixture is heated under reflux for about one hour and then poured over crushed ice to yield crystals which are recrystallized from ethyl acetate to give the pure product, 4-n-butylphenylthiourea, m.p. 123°-25° C.

B. 3,4-Methylenedioxyphenylthiourea, m.p. 208°-210° C. (dec.)

C. 4-Methoxyphenylthiourea, m.p. 207°-210° C.

EXAMPLE X

This example, which illustrates another method of making the formula (XX) thioureas, involves the interaction of excess ammonia with an appropriate isothiocyanate, generally in an ethereal type solvent.

A. 1-(exo-2-Norbornyl)thiourea:

exo-2-Norbornylisothiocyanate [prepared by the method of Diveley et al., J. Org. Chem., 34, 616 (1969)] (27.17 g., 0.178 mole) in 200 ml dry monoglyme is treated with ammonia gas for 5 hrs. The mixture is let stand overnight. The product is separated by filtration and washed with ether to afford a solid, 1-(exo-2-norbornyl)thiourea, m.p. 181°-183° C.

B. N-(9-Fluorenyl)-thiourea:

To 16.52 g (0.074 mole) of 9-fluorenylisothiocyanate in ether is added excess anhydrous $NH_3$ with cooling. The reaction mixture is capped and allowed to stand overnight at 0° C. Filtration gives the product, N-(9-fluorenyl)-thiourea, m.p. (158°) 182°-189° C.

C. By following the foregoing procedures of this example, except that an equivalent quantity of an appropriate isothiocyanate is reacted with excess ammonia, the following are obtained as respective products:

2-(Bicyclo[2.2.2.]octyl)thiourea;
endo-2-(Bicyclo[3.2.1.]octyl)thiourea;
anti-7-norbornenylthiourea;
1- and 2-(2,3,3a,4,5,6,7,7a-octahydro-4,7-methanoindanyl)thioureas;
3-(2,3,6,6a-Tetrahydro-1H-1,3a-ethanopentalenyl)thiourea;
5-(3a,4,5,6,7,7a-hexahydro-4,7-methanoindenyl)thiourea;
1,1-Dimethylphenethylthiourea;
d-α-phenethylthiourea;
1-α-phenethylthiourea;
1-Benzylcyclopentylthiourea;
1-Bicyclo[4.2.0.]octa-1,3,5-trienylthiourea;
1-Adamantylmethylthiourea;
2-Adamantylthiourea;
cis-2-Phenylcyclopentylthiourea;
cis-2-Phenylcycloheptylthiourea and
cis-2-Cyclohexylcyclopentylthiourea.

EXAMPLE XI

A. Methyl N-(9-fluorenyl)carbamimidothioate Hydroiodide:

To 7.85 g. (0.033 mole) of N-(9-fluorenyl)thiourea in 200 ml acetone is added 4.68 g (0.033 mole) of methyl iodide. The mixture is allowed to stand at room temperature for about 4 hours. Ether (400 ml) is added and the mixture allowed to stand overnight, affording the crystalline product, methyl N-(9-fluorenyl)carbamimidothioate hydroiodide, which is filtered off; m.p. (208) 212°-14° C.

B. The foregoing S-methylation procedure of Example XI-A is followed, except that an equivalent quantity of an appropriate thiourea is reacted with methyl iodide in the indicated molar ratios, respectively, and using the indicated solvent reaction medium to yield the following products of formula (XXI) as the hydroiodide salt:

C. By repeating the foregoing S-methylation procedure of Example XI-A, but using an equivalent amount of each thiourea obtained from Example X-C in methanol as the reaction solvent and with a slight stoichiometric excess of methyl iodide, the corresponding carbamimidothioate hydroiodides of formula (XXI) are obtained.

$$\underset{RN=C-NH_2 \cdot HI}{\overset{SMe}{|}} \quad (XXI)$$

| R | Solvent | Ratio of Reactants | m.p. (°C.) |
|---|---|---|---|
| exo-2-norbornyl | acetone | 1:1.1 | (oil) |
| p-n-Bu—Ph | acetone | 1:1 | 77–79 |
| 9-fluorenyl | acetone | 1:1 | (201) 212–14 |
| 1-naphthyl | $CH_2Cl_2$—MeOH (4:1) | 1:1 | 191–192 |
| m-$CF_3$—Ph | acetone | 1:1 | 120–22 |
| m-MePh | acetone | 1:1.5 | 145–50 |
| 3,4-diOMe-Ph | MeOH | 1:4 | 186–193 |
| p-PhCH$_2$O—Ph | acetone | 1:2.2 | (195) 198–202 |
| 3,4-CH$_2$⟨O—Ph—O⟩ | MeOH | 1:1 | 138–138.5 |

-continued $$\underset{RN=C-NH_2 \cdot HI}{\overset{SMe}{|}} \quad (XXI)$$

| R | Solvent | Ratio of Reactants | m.p. (°C.) |
|---|---|---|---|
| 3-OMePh | acetone | 1:1.5 | 119–123 |
| 3-Cl—Ph | MeOH | 1:1.1 | (120) 125–129 |
| 4-NO$_2$—Ph | MeOH | 1:2 | 190–197 dec. |
| 4-OMePh | acetone | 1:1.1 | 161–164 |
| 4-SMePh | acetone | 1:1 | 158–160 |
| 4-NMe$_2$—Ph | MeOH | 1:1 | 166–168 |
| 3-Pyridyl | acetone | 1:1 | 98–100 (free base) |
| 4-MePh | MeOH | 1:1 | 129–130.5 |

EXAMPLE XII

A. N-(4-Tolyl)-1-pyrrolidinecarboximidamide Hydroiodide:

4-Tolylthiourea (33.2 g., 0.2 mole) in 200 ml. acetone is heated under reflux for 3 hrs. with methyliodide (31.4 g., 0.221 mole). Solvent is removed in vacuo and the resulting 2-methyl-1-(4-tolyl)-2-thiopseudourea hydroiodide dissolved in 200 ml. tert-butanol. Pyrrolidine (28.4 g., 0.4 mole) is added and the mixture heated at reflux for 18 hrs. The reaction mixture is cooled, diluted with ether and the resulting solid separated. Recrystallization from acetone-ether affords N-(4-tolyl)-1-pyrrolidinecarboximidamide hydroiodide, m.p. 166°–168°

C. Conventional treatment of the salt in CH$_2$Cl$_2$ with aqueous (10–20%) NaOH affords the corresponding free base.

B. N-2,6-Dichlorophenyl-1-pyrrolidinecarboximidamide Hydrochloride:

A mixture of 14.52 g (0.04 mol) of methyl N-2,6-dichlorophenylcarbamimidothioate hydroiodide and 5.69 g (0.08 mol) of dry pyrrolidine in 30 ml of t-BuOH is heated under reflux for 3 days. The solvent is removed in vacuo and the resultant non-crystalline hydroiodide salt is converted to the free base in CH$_2$Cl$_2$ with cold 20% NaOH followed by drying (K$_2$CO$_3$), solvent removal, and conversion of the base to the HCl salt in isopropanol using anhydrous HCl. Recrystallization from isopropanol, using sufficient MeOH to effect solution, gives the pure product, N-2,6-dichlorophenyl-1-pyrrolidinecarboximidamide hydrochloride, m.p. 292°–295° C.

C. The foregoing procedures of Examples XII-A and B are followed, except that an equivalent amount of an appropriate methylthio hydroiodide of formula (XXI) is reacted with an appropriate amine (HNR$_4$R$_5$) in the indicated molar ratio, respectively, with or without an additional equivalent of Et$_3$N as indicated, in refluxing tert-butanol to yield the following respective guanidines, isolated either as the free base or as the indicated acid addition salt:

$$\underset{RN=C-NH_2 \cdot HX}{\overset{NR_4R_5}{|}}$$

| R | —NR$_4$R$_5$ | HX | Molar Ratio | Added Base | m.p. (°C.) |
|---|---|---|---|---|---|
| Ph |  | HBr | 1:1.1 | Et$_3$N | 203–205 |
| 3,4-CH$_2$ 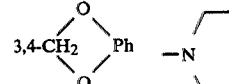 Ph | 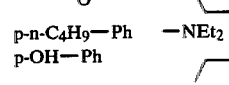 | HI | 1:2 | — | 171–172.5 |
| p-n-C$_4$H$_9$—Ph | —NEt$_2$ | fumarate | 1:2 | — | 96–98 |
| p-OH—Ph | 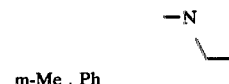 | HI | 1:2 | — | 216–218 |
| m-Me . Ph | 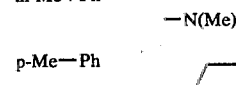 | cyclamate | 1:1.06 | Et$_3$N | 170–172 |
| p-Me—Ph | 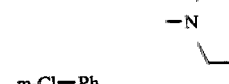 | HI | 1:2 | — | 166–168 |
| m-Cl—Ph | 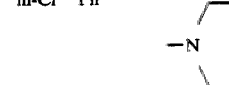 | base | 1:2 | — | 143.5–145.5 |
| 2,6-diCl—Ph | 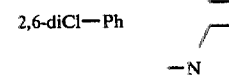 | HCl | 1:2 | — | 292–295 |
| Ph |  | HI | 1:2 | — | 175–177 |

-continued $$RN=\underset{\underset{\displaystyle NR_4R_5}{|}}{C}-NH_2 \cdot HX$$

| R | —NR₄R₅ | HX | Molar Ratio | Added Base | m.p. (°C.) |
|---|---|---|---|---|---|
| Ph | —N(piperidinyl) | HNO₃ | 1:2 | — | 139–141 |
| p-NO₂—Ph | —N(piperidinyl) | HI | 1:2 | — | 240–242 (dec.) |
| (Ph)₂CH | —N(morpholinyl) | base | 1:2 | — | 122–124 |
| Ph | —N(Me)(cyclopentyl) | HI | 1:1.3 | Et₃N | 149–152 |
| p-Me—Ph | —N(pyrrolidinyl) | HI | 1:2 | — | 166–168 |
| (Ph)₂CH | —N(pyrrolidinyl) | HI | 1:2 | — | 205–206 |
| exo-2-norbornyl | —N(piperidinyl) | HI | 1:2 | — | 160–163 |
| " | —N(morpholinyl) | HI | 1:2 | — | 198–199.5 |
| Ph | —N(pyrrolidinyl) | HCl | 1:2 | — | 181–184 |
| 3,4-diMeO—Ph | —N(pyrrolidinyl) | HI | 1:2 | — | 221–222 |
| m-CF₃—Ph | —N(Me)(cyclopentyl) | fumarate | 1:1.3 | Et₃N | 150–153 |
| 1-naphthyl | —N(Me)(cyclohexyl) | base | 1:2 | — | 132–133 |
| " | —NEt₂ | fumarate | 1:4 | — | 208–210 (dec.) |
| 9-fluorenyl | —N(piperidinyl) | HI | 1:2 | — | 247–249 (dec.) |
| 1-naphthyl | —N(pyrrolidinyl) | HI | 1:2 | — | 209–211 |
| 2,6-diMe-Ph | —N(pyrrolidinyl) | HI | 1:2 | — | 191–192 |
| 4-PhCH₂O—Ph | —N(pyrrolidinyl) | tosylate | 1:2.1 | — | 187–190 |

-continued $$RN=C(NR_4R_5)-NH_2 \cdot HX$$

| R | —NR₄R₅ | HX | Molar Ratio | Added Base | m.p. (°C.) |
|---|---|---|---|---|---|
| 3-OMe—Ph | —N(piperidine) | fumarate | 1:2 | — | 187–189 |
| 4-OMe—Ph | N(Me)—cyclohexyl | base | 1:2 | — | 120–122 |
| 4-OMe—Ph | N(H)—CH₂—phenyl | base | 1:2 | — | 134–135 |
| 4-SMe—Ph | —N(morpholine) | HI | 1:1.1 | Et₃N(l) | 174–175.5 |
| 4-NMe₂Ph | —N(piperidine) | base | 1:2 | — | (111)117–119 |
| 4-NMe₂Ph | —N(piperidine) | HCl | — | — | 206–207 dec. |
| Ph | —N(2,6-dimethylpiperazine) | 2 HI | 1:2.4 | — | 266 dec. |
| 3-Pyridyl | —N(morpholine) | base | 1:2.1 | — | 188–190 |
| 3,4-CH₂O₂—Ph | —N(Me)—cyclohexyl | base | 1:2 | — | 121.5–123 |
| 4-Me—Ph | —N(morpholine) | HI | 1:2 | — | 197–204 |
| 4-Me—Ph | —N(thiomorpholine) | base | 1:1.2 | Et₃N(l) | 119–120 |
| 4-Me—Ph | —N(thiomorpholine) | HOAc | — | — | 119–123 polymer (133)134–137 |
| 3-Me—Ph | —N(thiomorpholine) | base | 1:1 | Et₃N(l) | 105 |
| 3-OMe—Ph | —N(Me)—cyclopentyl | base | 1:2.6 | Et₃N(2.6) | 93–95 |
| 3-Me—Ph | —N(morpholine) | HI | 1:2 | — | (160)168–191 |
| 3-OMe—Ph | —N(thiomorpholine) | HI | 1:1.2 | Et₃N(l) | (188)189–192 |

D. Each of the foregoing acid addition salts obtained in Example XII-C is converted to the corresponding free base by conventional treatment with alkali.

EXAMPLE XIII

N-Phenyl-1-pyrrolidinecarboximidamide Hydrochloride:

To 1.74 g (0.01 mole) of phenyl isocyanide dichloride is added 0.71 g (0.01 mole) of pyrrolidine and 1.01 g (0.01 mole) of triethylamine under $N_2$ in dry ether with stirring and cooling. The resulting mixture is allowed to stir for ½ hr and the resultant $Et_3N\cdot HCl$ is filtered. The filtrate is added to a saturated solution of anhydrous $NH_3$ in isopropanol. The resulting $NH_4Cl$ is filtered and the filtrate is concentrated in vacuo to remove excess ammonia, followed by the addition of dry HCl resulting in crystalline product, N-phenyl-1-pyrrolidinecarboximidamide hydrochloride, m.p. 181°–84° C. after crystallization from methanol-isopropanol.

EXAMPLE XIV

N-(1-Methyl-2-pyrrolidinylidene-N'-phenyl-1-pyrrolidinecarboximidamide L-(+)-Tartrate:

To 1.84 g (0.013 mole) of boron trifluoride etherate in $Et_2O$ (anhydrous) under $N_2$ is added 1.02 g (0.011 mole) of epichlorohydrin with rapid stirring for 3 hrs. The resulting crystalline triethyloxonium fluoborate is washed with fresh anhydrous ether by decantation under $N_2$. The crystals are dissolved in dry $CH_2Cl_2$. To the solution is added 1.09 g (0.011 mole) of 1-methyl-2-pyrolidinone and the mixture is stirred for 2 hrs. To the resulting solution is added 0.01 mole of N-phenyl-1-pyrrolidinecarboximidamide with cooling in an ice-water bath. The reaction mixture is allowed to stir overnight (ca. 16 hrs). The mixture is taken to dryness in vacuo and then diluted with ether affording crude crystalline $HBF_4$ salt of N-(1-methyl-2-pyrrolidinylidene)-N'-phenyl-1-pyrrolidinecarboximidamide. The crystals are recrystallized from acetone to give pure fluoborate salt); m.p. 164°–166° C. The fluoborate salt is converted to the free base in $CH_2Cl_2$ with NaOH (20%) in ice. The organic layer is dried over anhydrous $K_2CO_3$, then filtered and taken to dryness in vacuo affording the free base. To the free base in MeOH is added an equimolar amount of L-(+)-tartaric acid. The resulting solution is concentrated while adding isopropanol until substantially all MeOH has evaporated off affording the tartrate salt upon cooling. Recrystallization from isopropanol with a small amount of MeOH affords the pure product, N-(1-methyl-2-pyrrolidinylidene)-N'-phenyl-1-pyrrolidinecarboximidamide L-(+)-tartrate, m.p. 153.5°–156° C.

EXAMPLE XV

By following the procedure of Example XIV, except that an appropriate lactam fluoborate of formula (IIIa) is reacted with an appropriate guanidine of formula (IV) in the molar ratio indicated, respectively, the following compounds of formula (I) are obtained and isolated as either free base or the indicated acid addition salt:

| Compound No. | n | R | $R_1$ | $R_2$ | $R_3$ | $NRR_5$ | Molar Ratio (III):(IV) | Form of Product | m.p. (°C.) |
|---|---|---|---|---|---|---|---|---|---|
| 1. | 1 | —$CHPh_2$ | Me | H | H | —N(pyrrolidinyl) | 1.1:1 | HI | 218–220 |
| 2. | 1 | Ph | Me | H | H | NHPh | 1.2:1 | base | 180–183 |
| 3. | 1 | Ph | Me | Me | H | —N(pyrrolidinyl) | 1:1 | HI | 158–160 |
| 4. | 1 | Ph | Me | H | Ph | —N(pyrrolidinyl) | 1:1 | HI | 215–217 |
| 5. | 1 | 1-naphthyl | Me | H | H | —N(pyrrolidinyl) | 1.2:1 | HI | 185–187 |
| 6. | 1 | Ph | Ph | H | H | —N(pyrrolidinyl) | 1.1:1 | HI | 193.5–194.5 |
| 7. | 1 | Ph | Me | H | H | —$NEt_2$ | 1.2:1 | HI | 155–157 |
| 8. | 1 | Ph | cyclohexyl | H | H | —N(pyrrolidinyl) | 1.1:1 | saccharinate | 165–166.5 |

-continued $$\begin{array}{c} R_3 \diagdown \quad (CH_2)_n \quad NR \\ \quad \quad \quad \quad \quad \quad \| \\ R_2 \diagup \quad \quad \quad \quad C-NR_4R_5 \\ \quad \quad N \quad =N \\ \quad \quad | \\ \quad \quad R_1 \end{array}$$

| Compound No. | n | R | $R_1$ | $R_2$ | $R_3$ | $NRR_5$ | Molar Ratio (III):(IV) | Form of Product | m.p. (°C.) |
|---|---|---|---|---|---|---|---|---|---|
| 9. | 1 | Ph | —CH$_2$Ph | H | H | —N⌒O (morpholino) | 1.2:1 | fumarate | 208–210 |
| 10. | 1 | Ph | —CH$_2$CH$_2$OH | H | H | —N⌒O (morpholino) | 1.2:1 | base | 128–130 |
| 11. | 1 | p-ClPh | Me | Ph | H | —NHPh | 1.1:1 | HCl | 204–207 |
| 12. | 1 | Ph | Me | Ph | H | —N⌒O (morpholino) | 1.08:1 | fumarate | (220)224–226 |
| 13. | 1 | 1-naphthyl | Me | H | H | —NEt$_2$ | 1.05:1 | fumarate | 187–189 |
| 14. | 1 | 9-Fluorenyl | Me | H | H | —N (pyrrolidino) | 1.1:1 | HI | 230–232 dec |
| 15. | 1 | Ph | —CH$_2$CH=CH$_2$ | H | H | —N (piperidino) | 1.2:1 | HClO$_4$ | 105.5–107 |
| 16. | 1 | Ph | Me | H | n-C$_8$H$_{17}$ | —N⌒O (morpholino) | 1:1 | tosylate | (130)133–135 |
| 17. | 1 | Ph | Me | H | n-C$_4$H$_9$ | —N (piperidino) | 1:1 | HI | 130–131 |
| 18. | 1 | p-nC$_4$H$_9$Ph | Me | H | H | —NEt$_2$ | 1.08:1 | fumarate | 163–165 |
| 19. | 1 | m-CF$_3$Ph | Me | H | H | —N(Me) (N-methylpyrrolidino) | 1.08:1 | fumarate | (135–137)139–141 |
| 20. | 2 | —CHPh$_2$ | Me | H | H | —N⌒O (morpholino) | 1:1 | L-(+)-tartrate | 146–148.5 |
| 21. | 1 | Ph | Me | H | H | —N(Me) (N-methylpyrrolidino) | 1.08:1 | HI | (120)128.5–130 |
| 22. | 1 | p-MePh | Me | H | H | —N (piperidino) | 1.2:1 | fumarate | 176–178 |
| 23. | 1 | 3,4CH$_2$O$_2$Ph | Me | H | H | —N (piperidino) | 1.17:1 | HI | 144–146 |
| 24. | 1 | m-ClPh | Me | H | H | —N⌒O (morpholino) | 2:1 | fumarate | 177.5–179.5 |

-continued structure: R3, R2 on a ring with N-R1, (CH2)n connecting to =N-C(=NR)-NR4R5

| Compound No. | n | R | R1 | R2 | R3 | NRR5 | Molar Ratio (III):(IV) | Form of Product | m.p. (°C.) |
|---|---|---|---|---|---|---|---|---|---|
| 25. | 1 | m-MePh | Me | H | H | —N(Me)⟨cyclopentyl⟩ | 1.2:1 | fumarate | 133–136 |
| 26. | 1 | 3,4-(OMe)₂Ph | Me | H | H | —N⟨pyrrolidinyl⟩ | 1.1:1 | phosphate | 201–204(dec.) |
| 27. | 1 | 4-PhCH₂O—Ph | Me | H | H | —N⟨pyrrolidinyl⟩ | 2.5:1 | HClO₄ | (151)152–154 |
| 28. | 1 | 3-OMePh | Me | H | H | —N⟨piperidinyl⟩ | 1.1:1 | HNO₃ | 104–109 |
| 29. | 1 | 4-OMePh | Me | H | H | —N(Me)⟨cyclohexyl⟩ | 2:1 | fumarate | 179–180.5 |
| 30. | 1 | 4-OMePh | Me | H | H | —N(H)CH₂⟨cyclohexyl⟩ | 2:1 | 0.5 fumarate | 208–209(dec.) |
| 31. | 1 | 4-SMePh | Me | H | H | —N⟨morpholinyl, O⟩ | 1.08:1 | HI | 142–144 |
| 32. | 1 | 4-NMe₂Ph | Me | H | H | —N⟨piperidinyl⟩ | 1.08:1 | HI | 171–172 |
| 33. | 1 | Ph | Me | H | H | —N⟨piperazinyl with Me, NH, Me⟩ | 1:1 | 2HI | 269–170(dec.) |
| 34 | 1 | 3-Pyridyl (Inverse Addn) | Me | H | H | —N⟨morpholinyl, O⟩ | 1:1.1 | 1.5 fumarate | 138–139.5 |
| 35. | 1 | Ph | n-C₈H₁₇ | H | H | —N⟨pyrrolidinyl⟩ | 1:1.1 | tartrate | oil |
| 36. | 1 | 3-C(O)CH₃Ph | Me | H | H | —N⟨pyrrolidinyl⟩ | 1:1.1 | pamoate | 158–164 (dec.) |

EXAMPLE XVI

N-(2,6-Dimethylphenyl)-N'-(1-methyl-2-pyrrolidinylidene)-1-pyrrolidinecarboximidamide Fumarate:

To a solution of 3.47 g (0.035 mole) of dry 1-methyl-2-pyrrolidinone in dry CH₂Cl₂ under dry N₂ is added 3.99 g (0.035 mol) of methyl fluorosulfonate. After 2 hrs., a solution of 6.52 g (0.03 mole) of N-(2,6-dimethylphenyl)-1-pyrrolidinecarboximidamide free base in dry CH₂Cl₂ is added at room temperature with stirring in one portion. After stirring overnight at ambient temperature, the reaction mixture is basified with excess cold NaOH (20%). The organic layer is separated and the aqueous phase is extracted with 2×50 ml of fresh CH₂Cl₂. The combined organic extracts, after drying over anhydrous K₂CO₃, are filtered and the solvent removed in vacuo. The residual oil is dissolved in ether and the solution filtered through diatomaceous earth. Treatment of the filtrate with a hot solution of fumaric acid in isopropanol to neutrality gives the product as the fumarate salt. Recrystallizations from isopropanol (filtering hot) gives the pure product, N-(2,6-dimethylphenyl)-N'-(1-methyl-2-pyrrolidinylidene)-1-pyrrolidinecarboximidamide fumarate, m.p. 182°–84° C. (slight dec.).

EXAMPLE XVII

The procedure of Example XVI is repeated, except that an appropriate guanidine of formula (IV) is substituted for the N-(2,6-dimethylphenyl)-1-pyrrolidinecarboximidamide used therein to react with the appropriate compound of formula (IIIb) in the molar ratio indicated, to yield the following respective products of formula (I), which are obtained and isolated as either free base or the indicated acid addition salt:

| Compound No. | R | $NR_4R_5$ | n | $R_1$ | Molar Ratio (IIIb) : (IV) | Form of Product | m.p. (°C.) |
|---|---|---|---|---|---|---|---|
| 1. | Ph | N⌒S (thiomorpholino) | 1 | Me | 1.09:1 | HI | 188–190 |
| 2. | Ph | $NHCH_2Ph$ | 1 | Me | 1.2:1 | fumarate | 130–132 |
| 3. | 1-naphthyl | " | 1 | Me | 1.2:1 | HI | 225–226 |
| 4. | p-$NO_2$—Ph | N(Me)-cyclohexyl | 1 | Me | 1:1 | base | 113–114.5 |
| 5. | 2,6-diCl—Ph | piperidino | 1 | Me | 1.14:1 | base | 139–141.5 |
| 6. | Ph | " | 1 | Me | 1:1 | L-(+)-tartrate | 153–155 |
| 7. | exo-2-norbornyl | " | 1 | Me | 1:1 | fumarate | 180–182 |
| 8. | 3,4-$CH_2O_2$—Ph (methylenedioxyphenyl) | N(Me)-cyclohexyl | 2 | Me | 1.2:1 | fumarate | (161-4)174 dec. |
| 9. | 4-MePh | morpholino (—N⌒O) | 1 | Me | 1.2:1 | HI | 190–191 dec. |
| 10. | 4-MePh | thiomorpholino (—N⌒S) | 1 | Me | 1.2:1 | HI | 166–168 dec. |
| 11. | 3-MePh | thiomorpholino (—N⌒S) | 1 | —$CH_2CH=CH_2$ | 1.17:1 | HI | 158–160 dec. |
| 12. | 3-OMePh | —N(Me)-cyclopropyl | 1 | —$CH_2CH=CH_2$ | 1.17:1 | fumarate . ½ $H_2O$ | 120–122 |
| 13. | 3-MePh | morpholino (—N⌒O) | 2 | Me | 1.2:1 | fumarate | (142–144)148–151 |
| 14. | 3-OMePh | thiomorpholino (—N⌒S) | 1 | Me | 1.2:1 | HI | 185–186 |
| 15. | 3-MePh | morpholino (—N⌒O) | 1 | Me | 1.2:1 | fumarate | 161–164 dec. |

EXAMPLE XVIII

This example illustrates methods of preparing the quaternary salts of the formula (I) compounds.

A.
N-(2,6-Dichlorophenyl)-N')-(1-methyl-2-pyrrolidinylidene)-1-pyrrolidinecarboximidamidinium Methofluorosulfonate:

To 6.83 g (0.02 mole) of N-(2,6-dichlorophenyl)-N'-(1-methyl-2-pyrrolidinylidene)-1-pyrrolidinecarboximidamide in dry $CH_2Cl_2$ is added 2.70 g (0.023 mole) of methyl fluorosulfonate with stirring under $N_2$. The mixture is stirred overnight and then taken to dryness in vacuo leaving an oily residue which is triturated with ether to give crystals. Recrystallization from acetone and then from ethyl acetate gives the pure product, N-(2,6-dichlorophenyl)-N'-(1-methyl-2-pyrrolidinylidene)-1-pyrrolidinecarboximidamidinium methofluorosulfonate, m.p. 148°–150° C.

B.
N-(1-Methyl-2-pyrrolidinylidene)-N'-phenyl-1-pyrrolidinecarboximidamidimium Methiodide:

A solution of (0.05 mole) of N-(1-methyl-2-pyrrolidinylidene-N'-phenyl-1-pyrrolidinecarboximidamide (Ex. ID) free base in 30 ml of acetone is treated with 0.05 mole of methyl iodide. After two days the crystals are collected and recrystallized from acetone affording pure N-(1-methyl-2-pyrrolidinylidene-N'-phenyl-1-pyrrolidinecarboximidamidinium methiodide, m.p. (156) 162°–164° C.

Anal. Calcd. for $C_{17}H_{25}N_4I$: C, 49.52; H, 6.11; N, 13.59. Found: C, 49.58; H, 6.11; N, 13.59.

C. Similarly, treatment of, the product of example (ID) as the free base (0.05 mole) in ether (dry) with methyl fluorosulfonate (0.05 mole) rapidly gives an oily precipitate which crystallizes. Recrystallization from t-BuOH gives the product of Example (XVIIIB) as the corresponding methofluorosulfonate salt, m.p. 135.5°–137° C.

EXAMPLE XIX

N-Phenyl-N'-(2-pyrrolidinylidene)-1-pyrrolidinecarboximidamide Hydroiodide:

A solution of 0.07 mole of triethyloxonium fluoborate in dry $CH_2Cl_2$ is prepared in the usual way. To this solution is added 6.08 g (0.070 mole) of 2-pyrrolidinone. After stirring for 2½ hrs., the mixture is basified with NaOH (50%) with cooling (ice-water bath). The organic layer is separated and dried over $K_2CO_3$, then filtered and treated with 12.28 g (0.065 mole) of N-phenyl-1-pyrrolidinecarboximidamide. The $CH_2Cl_2$ solvent is evaporated while replacing with tert-butanol and the resulting solution refluxed for 22 hrs. The reaction mixture is allowed to cool to room temperature and then neutralized with HI (47%), affording crystals of crude HI salt. Recrystallization from tert-butanol gives pure salt, N-phenyl-N'-(2-pyrrolidinylidene)-1-pyrrolidinecarboximidamide hydroiodide, m.p. 223°–225° C. dec.

EXAMPLE XX

N-(1-Methyl-2-pyrrolidinylidene)-N'-phenyl-1-pyrrolidinecarboximidamide L-(+)-Tartrate:

To 1.74 g (0.01 mole) of phenyl isocyanide dichloride in dry $Et_2O$ with cooling under $N_2$ is added 0.71 g (0.01 mole) of pyrrolidine followed by 1.01 g (0.01 mole) of $Et_3N$ with stirring. The mixture is allowed to stir for 1½ hrs. and then filtered to remove precipitated $Et_3N.HCl$. To the filtrate is added 1.96 g (0.02 mole) of 1-methyl-2-iminopyrrolidine in an ice-water bath. The resultant mixture is allowed to stir overnight under $N_2$ and then filtered to remove N-methyl-2-iminopyrrolidine hydrochloride, m.p. 182°–188° C. The filtrate is evaporated to dryness in vacuo affording in an oil which is dissolved in MeOH (10 ml) and treated with an equimolar amount of L(+)-tartaric acid. The resultant solution is concentrated while adding i-PrOH to give crystals. Recrystallization from isopropanol-acetonitrile gives the pure L-(+)-tartrate salt, N-(1-methyl-2-pyrrolidinylidene)-N'-phenyl-1-pyrrolidinecarboximidamide, m.p. 153°–56° C.

EXAMPLE XXI

N-(1-Methyl-2-pyrrolidinylidene)-N'-phenyl-1-pyrrolidinecarboximidamide L-(+)-Tartrate:

To 0.99 g (0.01 mole) of 1-methyl-2-pyrrolidone in dry benzene is added with stirring at reflux temperature 1.26 g (0.01 mole) of dimethyl sulfate slowly. The reaction mixture is allowed to stir for 5 hrs. To the mixture is added 1.89 g (0.01 mole) of N-phenyl-1-pyrrolidinecarboximidamide slowly. The resulting mixture is allowed to stir overnight at room temperature. The mixture is taken to dryness in vacuo and then dissolved in $CH_2Cl_2$ followed by conversion to the free base with NaOH (50%) in ice. The organic layer is dried ($K_2CO_3$), filtered and evaporated to dryness in vacuo affording 2.7 g of an oil. The oil is dissolved in MeOH followed by addition of 1.5 g (0.01 mole) of L(+)-tartaric acid. Recrystallization from methanol-isopropanol gives the product, N-(1-methyl-2-pyrrolidinylidene)-N'-phenyl-1-pyrrolidinecarboximidamide L-(+)-tartrate, m.p. 153°–156° C.

EXAMPLE XXII

N-(1-Methyl-2-pyrrolidinylidene)-N'-phenyl-1-pyrrolidinecarboximidamide L-(+)-Tartrate:

To a cooled solution of 1.98 g (0.02 mole) of 1-methyl-2-pyrrolidone in dry toluene is added 3.95 g (0.04 mole) of phosgene. The resulting mixture is allowed to stir under $N_2$ to room temperature over 45 minutes to give white crystals. The excess $COCl_2$ and solvent are removed with the aid of a filter stick (under $N_2$). Fresh toluene is added, then removed under vacuum in order to remove residual phosgene. The crystals are washed in this way with fresh toluene two more times and then dissolved in dry $CH_2Cl_2$ followed by the addition of 1.89 g (0.01 mole) of N-phenyl-1-pyrrolidinecarboximidamide and 1.01 g (0.01 mole) of triethylamine. The resulting mixture is stirred overnight under $N_2$. The mixture is taken to dryness in vacuo, the residue dissolved in $CH_2Cl_2$ and the latter solution treated with NaOH (50%) in ice. The organic layer, which contains the free base form of the product, is separated, dried over anhydrous $K_2CO_3$, filtered and taken to dryness in vacuo affording an oily residue. The oil is dissolved in isopropanol followed by addition of L-(+)-tartaric acid to about pH 6-7. The resulting crystals are recrystallized from isopropanol to give pure product, N-(1-methyl-2-pyrrolidinylidene)-N'-phenyl-1-pyrrolidinecarboximidamide L-(+)-tartrate, m.p. 155°–156° C.

EXAMPLE XXIII

N-(1-Methyl-2-pyrrolidinylidene)-N'-phenyl-1-pyrrolidinecarboximidamide Hydroiodide:

To 2.57 g (0.01 mole) of 1-methyl-2-methylthio-1-pyrrolinium iodide in t-BuOH is added 1.89 g (0.01 mole) of N-phenyl-1-pyrrolidinecarboximidamide. The resulting mixture is allowed to heat under reflux overnight. Evolving MeSH is trapped in concentrated NaOH solution. Cooling and scratching gives 3.65 g (92%) of crude product which upon recrystallization from t-BuOH gives pure N-(1-methyl-2-pyrrolidineylidene-N'-phenyl-1-pyrrolidinecarboximidamide hydroiodide, m.p. 206°–207° C., identical in all respects with the product of Example (ID)

EXAMPLE XXIV

N-(1-Methyl-2-pyrrolidinylidene-N'-phenyl-1-pyrrolidinecarboximidamide L(+)-Tartrate:

To 1.29 g (0.0075 mole) of 2,2-diethoxy-1-methylpyrrolidine in dry benzene is added 1.42 g (0.0075 mole) of N-phenyl-1-pyrrolidinecarboximidamide. The mixture, after refluxing overnight, is taken to dryness in vacuo. The residue is treated with dilute hydrochloric acid (10%) then basified with cold NaOH (20%) and the free product is extracted with ether. The dried ($K_2CO_3$) extracts are taken to dryness in vacuo and the residual oil is taken up in i-PrOH and treated with one mole equivalent of L-(+)-tartaric acid. After recrystallization from MeOH-i-PrOH, pure N-1-methyl-2-pyrrolidinylidene-N'-phenyl-1-pyrrolidinecarboximidamide L(+)tartrate is obtained; m.p. 153°–156° C.

EXAMPLE XXV

N-(1-Methyl-2-pyrrolidinylidene)-N'-phenyl-1-pyrrolidinecarboximidamide is converted to the following organic and inorganic pharmaceutically acceptable acid addition salts by conventional treatment with each of the respective indicated acids:
fumarate, m.p. 156°–57° C.;
phosphate, m.p. 200°–01° C. (dec.);
hydrobromide, m.p. (206) 207°–09° C.;
oxalate, m.p. 129°–31° C.;
pamoate, m.p. 253°–56° C. (dec.);
nitrate, m.p. 170°–71° C. (slight dec.);
maleate, m.p. 115°–17° C.; and
p-hydroxybenzoate, m.p. 179°–80° C.

EXAMPLE XXVI

A. N-Phenyl-1-pyrrolidinecarboximidamide Hydrochloride; and

B. 1-(1-Methyl-2-pyrrolidinylidene)pyrrolidinium Iodide Hydrate

A. The mother liquor set aside in Example I-D is taken to dryness in vacuo and the residue is taken up in methylene chloride and basified with cold dilute NaOH. Extraction with $CH_2Cl_2$ (200 ml) is repeated three times. The combined organic extracts are dried over anhydrous $K_2CO_3$, filtered, and taken to dryness in vacuo, leaving a brown heavy sirup. Extraction of the sirup by trituration with hexane (2×200 ml) and with ether (3×200 ml) leaves a dark residue (set aside). The organics layers are combined and treated with charcoal, filtered, and taken to dryness in vacuo giving a brown sirup which is converted to the HCl salt and recrystalized from isopropanol-ether to give N-phenyl-1-pyrrolidinecarboximidamide hydrochloride, m.p. 181°–84° C.

Anal. Calc'd. for $C_{11}H_{15}N_3.HCl$: C, 58.53; H, 7.15%. Found: C, 58.59; H 7.08%.

B. The dark residue set aside above is taken up in isopropanol and treated with a large amount of charcoal. Filtration followed by solvent removal in vacuo gives a dark brown glassy material which, upon trituration with acetone with concommitant charcoaling, affords white crystals of 1-(1-methyl-2-pyrrolidinylidene)pyrrolidinium iodide which forms a hydrate with about ¼ mole $H_2O$; m.p. (98) 108°–110° C. On a humid day the crystals will take up excess water and melt but will solidify again when the humidity drops.

Anal. Calc'd. for $C_{19}H_{17}N_2^+.I^-.¼H_2O$: C, 37.98, H, 6.02, I, 44.58 $H_2O$, 1.58% $H_2O$, 1.13% Found: C, 38.15; H, 6.11; I, 45.25.

EXAMPLE XXVII

N-(4-Aminophenyl)-N'-(1-methyl-2-pyrrolidinylidene)-1-pyrrolidinecarboximidamide Hydrobromide:

N-(1-methyl-2-pyrrolidinylidene)-N'-(4-nitrophenyl)-1-pyrrolidinecarboximidamide (product 4 of Example XVII), 2.46 g (0.0078 mole) in 50 ml of absolute ethanol in hydrogenated (ca. 3 atmospheres) on a Parr shaker over Raney nickel catalyst. Uptake of hydrogen is complete after ca. 0.5 hr. The catalyst is separated by filtration and washed with ethanol. The combined filtrates are evaporated in vacuo. The residue is dissolved in ethanol and neutralized with one equivalent of aqueous HBr solution (48%). The resulting solid is recrystallized from ethanol-ether to give pure N-(4-aminophenyl)-N'-(1-methyl-2-pyrrolidinylidene)-1-pyrrolidinecarboximidamide hydrobromide, m.p. 241°–241.5° C.

Anal. Calcd. for $C_{16}H_{23}N_5HBr$: C, 52.46; H, 6.60; N, 19.12. Found: C, 52.44; H, 6.60; N, 19.09.

EXAMPLE XXVIII

N-(4-Acetylaminophenyl)-N'-(1-methyl-2-pyrrolidinylidene-1-pyrrolidinecarboximidamide Hydrobromide:

N-(4-aminophenyl-N'-(1-methyl-2-pyrrolidinylidene-1-pyrrolidinecarboximidamide (The product of Example XXVII) as its free base, 3.4 g (0.0119 mole) is heated on a steam bath with 25 ml of acetic anhydride for ca. 1 hr. After this time the reaction mixture is diluted with ethanol and heated for another hour. The volatile components are removed in vacuo and the residue is treated with dilute aqueous NaOH and extracted into methylene chloride. After drying the extracts over $K_2CO_3$, filtration and solvent removal affords a residual oil which is converted to its corresponding HBr acid addition salt in ether-ethanol. Recrystallization from ethanol-ether gives the pure product N-(4-Acetylaminophenyl)-N'-(1-methyl-2-pyrrolidinylidene-1-pyrrolidinecarboximidamide, m.p. 246°–247° C.

EXAMPLE XXIX

N-(1-Methyl-2-pyrrolidinylidene)-N'-(4-methylsulfonylphenyl)-4-morpholinecarboximidamide:

To 1.98 g (0.0006 mole) of N-(4-methylthiophenyl)-N'(1-methyl-2-pyrrolidinylidene)-4-morpholinecarboximidamide (compound 31 of Example XV) as the free base is dry methylene chloride, cooled to 0° , is added with stirring 3.6 g (0.018 mole) of m-chloroperoxybenzoic acid such that the temperature does not rise above 5° C. The mixture is allowed to stir at these temperatures for 0.5 hr. then is washed respectively with saturated solutions of $NaHCO_3$ (3×40 ml) and NaCl (3×35 ml). The organic layer is dried ($K_2CO_3$) then filtered (filter aid) followed by evaporation to near dryness in vacuo. Dilution with MeOH affords some insoluble material which is filtered off and discarded. The filtrate is evaporated to near dryness on the steam bath. Dilution with ether affords crystals, m.p. 160°–166° C. Recrystallization from ether gives pure N-(1-methyl-2-pyrrolidinylidene)-N'-(4-methylsulfonylphenyl)-4-morpholinecarboximidamide, m.p. (165) 167°–170° C.

Anal. Calcd. for $C_{17}H_{24}N_4O_3S$: C, 56.03; H, 6.64. Found: C, 56.05; H, 6.69.

EXAMPLE XXX

N-(1-Methyl-2-pyrrolidinylidene)-N'-(4-methylsulfinylphenyl)-4-morpholinecarboximidamide:

To a stirring solution of 1.98 g (0.006 mole) of N-(4-methylthiophenyl)-N'-(1-methyl-2-pyrrolidinylidene)-4-morpholinecarboximidamide (compound 31 of Example XV) as the free base in $CH_2Cl_2$ at 5° is added 1.22 g (0.006 mole) of m-chloroperoxybenzoic acid such that the temperature is maintained at 5°. The reaction mixture is then allowed to warm to room temperature and stirred for two more hours. The organic layer is washed respectively with saturated $NaHCO_3$ solution (3×30 ml) and saturated NaCl solution (2×30 ml) then dried over $K_2CO_3$ (anhyd). Filtration, solvent removal in vacuo, and treatment of the residue with ether-hexane gives the crude product which is recrystallized from ether-hexane to give pure N-(1-methyl-2-pyrrolidinylidene)-N'-(4-methylsulfinylphenyl)-4-morpholinecarboximidamide, m.p. (115)117°–120° C.

Anal. Calcd. for $C_{17}H_{24}N_4O_2S$: C, 58.60; H, 6.94. Found: C, 58.58, H, 6.91.

EXAMPLE XXXI

N-(4-Hydroxyphenyl)-N'-(1-methyl-2-pyrrolidinylidene)-1-pyrrolidinecarboximidamide Hydroiodide:

A solution of 26.6 g (0.071 mole) of N-(1-methyl-2-pyrrolidinylidene)-N'-(4-benzyloxyphenyl)-1-pyrrolidinecarboximidamide (product 27 of Example XV) as its corresponding free base in 50 ml of acetic acid is placed in a Parr shaker and hydrogenated at ca. 3 atmospheres over 10% Pd/C for ca. 2 hrs., or until $H_2$ uptake is complete, at room temperature. The reaction mixture is filtered and the solvent is removed in vacuo affording a viscous oil which is taken up in acetone and treated with one equivalent of HI (concentrated aqueous). The crude crystals are recrystallized from methanol-acetone-ether to give pure N-(4-hydroxyphenyl)-N'-(1-methyl-2-pyrrolidinylidene)-1-pyrrolidinecarboximidamide hydroiodide, m.p. 174°–178° C.

Anal. Calcd. for $C_{16}H_{22}N_4O.HI$: C, 46.39; H, 5.60; N, 13.52. Found: C, 46.62; H, 5.59; N, 13.63.

EXAMPLE XXXII

N-(4-Acetoxyphenyl)-N'-(1-methyl-2-pyrrolidinylidene)-1-pyrrolidinecarboximidamide Hydriodide:

Twelve grams (0.20 mole) of glacial acetic acid is added slowly to a solution of 5.15 g (0.0124 mole) of N-(4-hydroxyphenyl)-N'-1-methyl-2-pyrrolidinylidene)-1-pyrrolidinecarboximidamide hydriodide (the compound of Example XXXI) and 41.2 g (0.20 mole of N,N'-dicyclohexylcarbodiimide in 400 ml of acetone. The reaction mixture is stirred at room temperature under nitrogen for 3 days. N,N'-Dicyclohexylurea is removed by filtration and the filtrate concentrated to dryness in vacuo to give an amber oil. The several triturations with ether a yellow solid is obtained. Recrystallization from acetone-ether gives a white solid, m.p. (188)195°–197° C. Further recrystallization from methanol-acetone-ether affords pure N-(4-acetoxyphenyl)-N'-(1-methyl-2-pyrrolidinylidene)-1-pyrrolidinecarboximidamide Hydriodide as a white solid, m.p. 196°–199° C.

Anal. Calcd. for $C_{18}H_{24}N_4O_2.HI$: C, 47.38; H, 5.52; N, 12.28. Found: C, 47.31; H, 5.57; N, 12.26.

EXAMPLE XXXIII

Following the procedures of previous Examples I–XXXII, and using the appropriate starting materials disclosed therein, or taught in the prior art, the following compounds of formula (I) may be prepared:

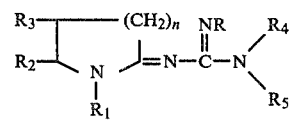

| Compound No. | n | R | $R_1$ | $R_2$ | $R_3$ | $-NR_4R_5$ |
|---|---|---|---|---|---|---|
| 1 | 3 | 4-SMePh | Me | H | H | —N(Me)⟨⟩ |
| 2 | 3 | 3-OMePh | Me | H | H | —N(Me)—◁ |
| 3 | 3 | 4-MePh | Me | H | H | —N⟨ |
| 4 | 3 | 3-ClPh | Me | H | H | —N(Me)Et |
| 5 | 3 | 4-FPh | Me | H | H | —N(Et)$_2$ |
| 6 | 3 | 4-OC(O)MePh | Me | H | H | —N⟨ |
| 7 | 3 | 2-naphthyl | Me | H | H | —N(Me)Et |
| 8 | 3 | 3-pyridyl | Me | H | H | —N(Me)—⟨⟩ |

-continued

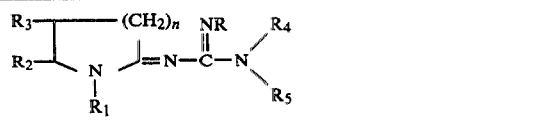

| Compound No. | n | R | $R_1$ | $R_2$ | $R_3$ | $-NR_4R_5$ |
|---|---|---|---|---|---|---|
| 9 | 3 | 2-thienyl | Me | H | H | —N⟨pyrrolidinyl⟩ |
| 10 | 3 | —CHPh$_2$ | Me | H | H | —N⟨pyrrolidinyl⟩ |
| 11 | 3 | 3,4-(OMe)$_2$Ph | Me | H | H | —N(Me)⟨cyclopentyl⟩ |
| 12 | 3 | 1-adamantyl | Me | H | H | —N(Me)$_2$ |
| 13 | 3 | —C(CH$_3$)$_2$CH$_2$C(CH$_3$)$_3$ (t-Octyl) | Me | H | H | —N⟨pyrrolidinyl⟩ |
| 14 | 3 | 9-fluorenyl | Me | H | H | —N(Me)$_2$ |
| 15 | 3 | 4-SMePh | Me | H | H | —N(Me)⟨cyclopentyl⟩ |
| 16 | 2 | 3-OMePh | Me | H | H | —N(Me)⟨cyclopentyl⟩ |
| 17 | 2 | 4-MePh | Me | H | H | —N(Me)⟨cyclohexyl⟩ |
| 18 | 2 | 3-ClPh | Me | H | H | —N⟨pyrrolidinyl⟩ |
| 19 | 2 | 4-FPh | Me | H | H | —N(Me)Et |
| 20 | 2 | 4-OC(O)MePh | Me | H | H | —N(Me)CH$_2$Ph |
| 21 | 2 | 1-naphthyl | Me | H | H | —N(Me)$_2$ |
| 22 | 2 | 3-pyridyl | Me | H | H | —N(Me)⟨cyclopentyl⟩ |
| 23 | 2 | 2-thienyl | Me | H | H | —N⟨pyrrolidinyl⟩ |
| 24 | 2 | —CH(Ph)$_2$ | Me | H | H | —N(Me)$_2$ |
| 25 | 2 | 3,4-CH$_2$⟨O,O⟩Ph | Me | H | H | —N(Me)CH$_2$Ph |
| 26 | 2 | 1-adamantyl | Me | H | H | —N(Me)Et |
| 27 | 2 | t-octyl | Me | H | H | —N⟨pyrrolidinyl⟩ |
| 28 | 2 | 9-fluorenyl | Me | H | H | —N(Me)Et |
| 29 | 2 | 3,4-(OMe)$_2$Ph | Me | H | H | —N(Me)⟨cyclohexyl⟩ |
| 30 | 2 | cyclohexyl | Me | H | H | —N(Et)$_2$ |
| 31 | 1 | 2-thienyl | CH$_2$CH=CH$_2$ (allyl) | H | H | —N⟨pyrrolidinyl⟩ |
| 32 | 1 | 2-furyl | Me | Me | H | —N(Me)⟨cyclohexyl⟩ |
| 33 | 1 | 4-SMePh | CH$_2$CH$_2$OH | H | H | —N(Me)⟨cyclopentyl⟩ |
| 34 | 1 | 3-OMePh | Me | n-Bu | H | —N(Me)Et |
| 35 | 1 | t-octyl | CH$_2$CH$_2$OH | H | H | —N(Et)$_2$ |
| 36 | 1 | 4-OC(O)—CH$_2$—CH(CH$_3$)$_2$Ph | Et | H | H | —N⟨pyrrolidinyl⟩ |
| 37 | 1 | 3,4-(OMe)$_2$Ph | CH$_2$Ph | H | H | —N(Me)$_2$ |

-continued

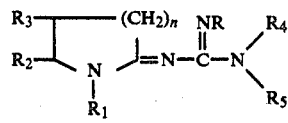

| Compound No. | n | R | R₁ | R₂ | R₃ | —NR₄R₅ |
|---|---|---|---|---|---|---|
| 38 | 1 | 3-pyridyl | allyl | H | H | —N(Me)—cyclohexyl |
| 39 | 1 | 6-OMe-3-pyridyl | Me | Me | H | —N(Me)—cyclopentyl |
| 40 | 1 | 6-Cl-3-pyridyl | Me | H | Me | —N(Et)₂ |
| 41 | 1 | 2,6-diCl-3-pyridyl | Me | H | H | —N(pyrrolidinyl) |
| 42 | 1 | 2,6-(Me)₂pyridyl | CH₂CH₂OH | H | H | —N(Me)—cyclopentyl |
| 43 | 1 | 2,6-(OMe)₂pyridyl | CH₂Ph | H | H | —N(Me)—cyclopentyl |
| 44 | 1 | 3,4-CH₂-(O,O)Ph (methylenedioxyphenyl) | cyclohexyl | H | H | —N(Me)Et |
| 45 | 1 | 3-C(O)MePh | Et | H | H | —N(Me)—cyclohexyl |
| 46 | 1 | 3-OMePh | Me | H | H | —N(pyrrolidinyl) |
| 47 | 1 | t-butyl | Me | Me | H | —N(CH₃)—cyclopentyl |
| 48 | 1 | 2-bicyclo[2.2.2]-octyl | Me | H | H | —N(pyrrolidinyl) |
| 49 | 1 | anti-7-norbornenyl | Me | H | H | —N(pyrrolidinyl) |
| 50 | 1 | endo-bicyclo[3.2.1]octyl | Me | H | H | —N(pyrrolidinyl) |
| 51 | 1 | α,α-(Me)₂benzyl | Me | H | H | —N(pyrrolidinyl) |
| 52 | 1 | α,α-(CH₂)₄CCH₂Ph | Me | H | H | —N(pyrrolidinyl) |
| 53 | 1 | tetrahydronaphthyl | Me | H | H | —N(pyrrolidinyl) |
| 54 | 1 | cyclohexyl/cyclopentyl | Me | H | H | —N(pyrrolidinyl) |
| 55 | 1 | phenyl-cyclopentyl | Me | H | H | —N(pyrrolidinyl) |
| 56 | 3 | 4-SMePh | Me | H | H | —N(piperidinyl) |

-continued

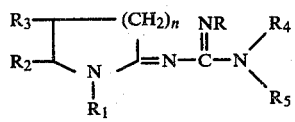

| Compound No. | n | R | $R_1$ | $R_2$ | $R_3$ | $-NR_4R_5$ |
|---|---|---|---|---|---|---|
| 57 | 3 | 3-ClPh | Me | H | H | —N⟨piperidine⟩ |
| 58 | 3 | 4-FPh | Me | H | H | —N⟨piperidine⟩ |
| 59 | 3 | 3-MePh | Me | H | H | —N⟨piperidine⟩ |
| 60 | 3 | 3,4-(OMe)$_2$Ph | Me | H | H | —N⟨piperidine⟩ |
| 61 | 2 | Ph | Me | H | H | —N⟨piperidine⟩ |
| 62 | 2 | t-octyl | Me | H | H | —N⟨piperidine⟩ |
| 63 | 2 | 2,6-(Me)$_2$Ph | Me | H | H | —N⟨piperidine⟩ |
| 64 | 2 | 2-thienyl | Me | H | H | —N⟨piperidine⟩ |
| 65 | 2 | 2-furyl | Me | H | H | —N⟨piperidine⟩ |
| 66 | 2 | 3-pyridyl | Me | H | H | —N⟨piperidine⟩ |
| 67 | 2 | 6-Cl-3-pyridyl | Me | H | H | —N⟨piperidine⟩ |
| 68 | 2 | 2,6-(Me)$_2$pyridyl | Me | H | H | —N⟨piperidine⟩ |
| 69 | 2 | 2,6-(OMe)$_2$pyridyl | Me | H | H | —N⟨piperidine⟩ |
| 70 | 2 | 9-flourenyl | Me | H | H | —N⟨piperidine⟩ |

-continued

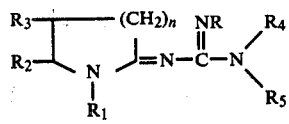

| Compound No. | n | R | $R_1$ | $R_2$ | $R_3$ | $-NR_4R_5$ |
|---|---|---|---|---|---|---|
| 71 | 2 | CH(Ph)$_2$ | Me | H | H | —N(piperidinyl) |
| 72 | 2 | 2-naphthyl | Me | H | H | —N(piperidinyl) |
| 73 | 2 | 3,4-(OMe)$_2$Ph | Me | H | H | —N(piperidinyl) |
| 74 | 2 | 4-FPh | Me | H | H | —N(piperidinyl) |
| 75 | 2 | 2,6-(Cl)$_2$Ph | Me | H | H | —N(piperidinyl) |
| 76 | 2 | cyclohexyl | Me | H | H | —N(piperidinyl) |
| 77 | 2 | 1-adamantylmethyl | Me | H | H | —N(piperidinyl) |
| 78 | 2 | 4-OC(O)MePh | Me | H | H | —N(piperidinyl) |
| 79 | 2 | α,α-(CH$_2$)$_4$CCH$_2$Ph | Me | H | H | —N(piperidinyl) |
| 80 | 2 | 3,4-CH$_2$(O,O)Ph | Me | H | H | —N(piperidinyl) |
| 81 | 1 | 4-SMePh | Me | Me | H | —N(piperidinyl) |
| 82 | 1 | 3,4-CH$_2$(O,O)Ph | Me | n-Bu | H | —N(piperidinyl) |
| 83 | 1 | t-octyl | Me | H | H | —N(piperidinyl) |
| 84 | 1 | 9-fluorenyl | Me | H | H | —N(piperidinyl) |

-continued

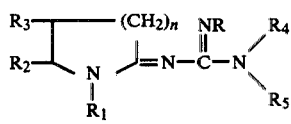

| Compound No. | n | R | R₁ | R₂ | R₃ | —NR₄R₅ |
|---|---|---|---|---|---|---|
| 85 | 1 | 1-naphthyl | Me | H | H | -N(piperidinyl) |
| 86 | 1 | 3-MePh | Me | H | Me | -N(piperidinyl) |
| 87 | 1 | phenyl | allyl | H | H | -N(piperidinyl) |
| 88 | 1 | 3,4-(OMe)₂Ph | cyclohexyl | H | H | -N(piperidinyl) |
| 89 | 1 | 4-FPh | Et | H | H | -N(piperidinyl) |
| 90 | 1 | 2,6-Cl₂Ph | Me | H | H | -N(piperidinyl) |
| 91 | 1 | 3,4-(Me)₂Ph | Me | H | H | -N(piperidinyl) |
| 92 | 1 | 2-thienyl | Me | Me | H | -N(piperidinyl) |
| 93 | 1 | 2-furyl | allyl | H | H | -N(piperidinyl) |
| 94 | 1 | 3-pyridyl | cyclohexyl | H | H | -N(piperidinyl) |
| 95 | 1 | α,α-(CH₂)₄CCH₂Ph | Me | H | H | -N(piperidinyl) |
| 96 | 1 | tetrahydronaphthyl | Me | H | H | -N(piperidinyl) |
| 97 | 1 | 1-adamantyl | CH₂CH₂OH | H | H | -N(piperidinyl) |
| 98 | 1 | t-octyl | CH₂CH₂OH | H | H | -N(piperidinyl) |

-continued $$R_3-\overset{(CH_2)_n}{\underset{R_2}{\overset{|}{C}}}\overset{NR}{\underset{N-C-N}{\overset{\|}{C}}}\overset{R_4}{\underset{R_5}{}}$$
$$\underset{R_1}{N}$$

| Compound No. | n | R | R₁ | R₂ | R₃ | —NR₄R₅ |
|---|---|---|---|---|---|---|
| 99 | 1 |  | Me | H | H |  piperidinyl |
| 100 | 1 | α,α-(Me)₂CCH₂Ph | Me | Me | H | piperidinyl |
| 101 | 3 | 4-SMePh | Me | H | H | morpholinyl |
| 102 | 3 | 3-ClPh | Me | H | H | morpholinyl |
| 103 | 3 | 4-FPh | Me | H | H | morpholinyl |
| 104 | 3 | 4-MePh | Me | H | H | morpholinyl |
| 105 | 3 | 3,4-(OMe)₂Ph | Me | H | H | morpholinyl |
| 106 | 3 | 3-pyridyl | Me | H | H | morpholinyl |
| 107 | 3 | 2-thienyl | Me | H | H | morpholinyl |
| 108 | 3 | 2-furyl | Me | H | H | morpholinyl |
| 109 | 3 | t-octyl | Me | H | H | morpholinyl |
| 110 | 3 | α,α-(Me)₂Benzyl | Me | H | H | morpholinyl |
| 111 | 3 | exo-2-norbornyl | Me | H | H | morpholinyl |
| 112 | 2 | 3,4-CH₂ (methylenedioxy)Ph | Me | H | H | morpholinyl |

-continued
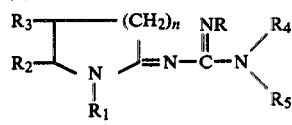
| Compound No. | n | R | $R_1$ | $R_2$ | $R_3$ | $-NR_4R_5$ |
|---|---|---|---|---|---|---|
| 113 | 2 | 1-adamantyl | Me | H | H | 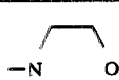 |
| 114 | 2 | ⬡ | Me | H | H | 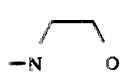 |
| 115 | 2 | 9-fluorenyl | Me | H | H | 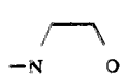 |
| 116 | 2 | neopentyl | Me | H | H | 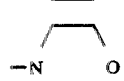 |
| 117 | 2 | ⬠–Ph | Me | H | H | 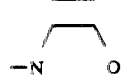 |
| 118 | 2 | ⬠–⬡ | Me | H | H | 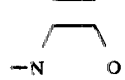 |
| 119 | 2 | α,α-$(CH_2)_4CCH_2Ph$ | Me | H | H | 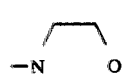 |
| 120 | 2 | α,α-$(Me)_2$Benzyl | Me | H | H | 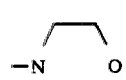 |
| 121 | 2 | endo-2-norbornyl | Me | H | H | 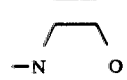 |
| 122 | 2 | 3,4-$(OMe)_2$Ph | Me | H | H | 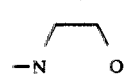 |
| 123 | 2 | 3,5-$Cl_2$Ph | Me | H | H | 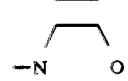 |
| 124 | 2 | 2-thienyl | Me | H | H | 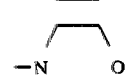 |
| 125 | 2 | 2-furyl | Me | H | H | 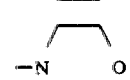 |
| 126 | 2 | 4-FPh | Me | H | H | 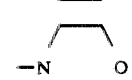 |

-continued

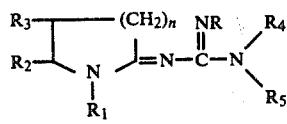

| Compound No. | n | R | $R_1$ | $R_2$ | $R_3$ | $-NR_4R_5$ |
|---|---|---|---|---|---|---|
| 127 | 2 | 4-NO$_2$Ph | Me | H | H | morpholino |
| 128 | 2 | 4-OC(O)MePh | Me | H | H | morpholino |
| 129 | 2 | 4-SMePh | Me | H | H | morpholino |
| 130 | 2 | 3-CF$_3$Ph | Me | H | H | morpholino |
| 131 | 2 | 2,6-(Me)$_2$Ph | Me | H | H | morpholino |
| 132 | 2 | 4-NEt$_2$Ph | Me | H | H | morpholino |
| 133 | 2 | 2-naphthyl | Me | H | H | morpholino |
| 134 | 2 | 2,6-(Me)$_2$Ph | Me | H | H | morpholino |
| 135 | 2 | 4-OC(O)EtPh | Me | H | H | 2,6-dimethylmorpholino |
| 136 | 1 | cyclohexyl | Me | H | H | morpholino |
| 137 | 1 | 9-fluorenyl | Me | H | H | morpholino |
| 138 | 1 | cyclopentyl-cyclohexyl | Me | H | H | morpholino |
| 139 | 1 | Ph, cyclopentyl | Me | H | H | morpholino |
| 140 | 1 | anti-7-norbornenyl | Me | H | H | morpholino |

-continued

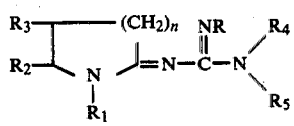

| Compound No. | n | R | $R_1$ | $R_2$ | $R_3$ | $-NR_4R_5$ |
|---|---|---|---|---|---|---|
| 141 | 1 | (1,2,3,4-tetrahydronaphthyl) | Me | H | H | -N(morpholino)O |
| 142 | 1 | 1-adamantylmethyl | Me | H | H | -N(morpholino)O |
| 143 | 1 | 2,2-$(CH_2)_4CCH_2Ph$ | Me | H | H | -N(morpholino)O |
| 144 | 1 | α,α-$(Me)_2$benzyl | Me | H | H | -N(morpholino)O |
| 145 | 1 | d-α-(1-naphthyl)ethyl | Me | H | H | -N(morpholino)O |
| 146 | 1 | (methylnorbornenyl) | Me | H | H | -N(morpholino)O |
| 147 | 1 | $CH_2Ph$ | Me | H | H | -N(morpholino)O |
| 148 | 1 | 4-FPh | Me | Me | H | -N(morpholino)O |
| 149 | 1 | 3-Br-4-ClPh | allyl | H | H | -N(morpholino)O |
| 150 | 1 | 3,4-$(OMe)_2Ph$ | Me | n-Bu | H | -N(morpholino)O |
| 151 | 1 | 3,4 $CH_2O_2$Ph (methylenedioxyphenyl) | Et | H | H | -N(morpholino)O |
| 152 | 1 | 2,6-$(Me)_2Ph$ | Me | Me | H | -N(morpholino)O |
| 153 | 1 | 6-Me-3-pyridyl | Me | H | H | -N(morpholino)O |
| 154 | 1 | 6-OMe-3-pyridyl | allyl | H | H | -N(morpholino)O |

-continued
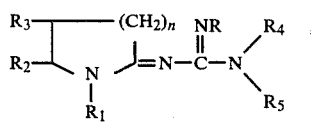
| Compound No. | n | R | $R_1$ | $R_2$ | $R_3$ | $-NR_4R_5$ |
|---|---|---|---|---|---|---|
| 155 | 1 | 6-Cl-3-pyridyl | Et | H | H | -N⏜O (morpholino) |
| 156 | 1 | 2,6-(Me)$_2$-3-pyridyl | Me | H | H | -N⏜O |
| 157 | 1 | 2,6-(OMe)-3-pyridyl | —CH$_2$CH=CHCH$_3$ | H | H | -N⏜O |
| 158 | 1 | 2,6-Cl$_2$-3-pyridyl | Me | H | H | -N⏜O |
| 159 | 1 | 2-thienyl | Me | H | H | -N⏜O |
| 160 | 1 | 2-furyl | Et | H | H | -N⏜O |
| 161 | 1 | OC(O)MePh | cyclohexyl | H | H | -N⏜O |
| 162 | 1 | 4-N(Me)$_2$Ph | Me | n-Bu | H | -N⏜O |
| 163 | 1 | 4-NO$_2$Ph | Me | H | H | -N⏜O |
| 164 | 1 | 4-OCH$_2$PhPh | Me | H | H | -N⏜O |
| 165 | 1 | 3-CF$_3$Ph | Me | H | H | -N⏜O |
| 166 | 3 | 4-SMePh | Me | H | H | -N⏜S (thiomorpholino) |
| 167 | 3 | 3-ClPh | Me | H | H | -N⏜S |
| 168 | 3 | 4-FPh | Me | H | H | -N⏜S |

-continued
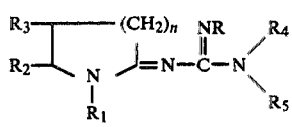
| Compound No. | n | R | R₁ | R₂ | R₃ | —NR₄R₅ |
|---|---|---|---|---|---|---|
| 169 | 3 | 3-CF₃Ph | Me | H | H | —N⌒S |
| 170 | 3 | 4-OC(O)MePh | Me | H | H | —N⌒S |
| 171 | 3 | 2-naphthyl | Me | H | H | —N⌒S |
| 172 | 3 | 3,4-(OMe)₂Ph | Me | H | H | —N⌒S |
| 173 | 3 | 3,4-CH₂(O,O)Ph | Me | H | H | —N⌒S |
| 174 | 3 | t-octyl | Me | H | H | —N⌒S |
| 175 | 3 | 2-thienyl | Me | H | H | —N⌒S |
| 176 | 3 | 2-furyl | Me | H | H | —N⌒S |
| 177 | 3 | 6-Cl-3-Pyridyl | Me | H | H | —N⌒S |
| 178 | 3 | 6-OMe-3-Pyridyl | Me | H | H | —N⌒S |
| 179 | 3 | 6-Me-3-Pyridyl | Me | H | H | —N⌒S |
| 180 | 3 | 4-OC(O)CH(CH₃)₂Ph | Me | H | H | —N⌒S |
| 181 | 2 | 4-SMePh | Me | H | H | —N⌒S |
| 182 | 2 | 4-ClPh | Me | H | H | —N⌒S |

-continued

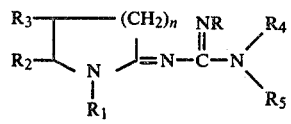

| Compound No. | n | R | R₁ | R₂ | R₃ | —NR₄R₅ |
|---|---|---|---|---|---|---|
| 183 | 2 | 3-BrPh | Me | H | H | thiomorpholino |
| 184 | 2 | 3-CF₃Ph | Me | H | H | thiomorpholino |
| 185 | 2 | 4-OC(O)MePh | Me | H | H | thiomorpholino |
| 186 | 2 | 1-naphthyl | Me | H | H | thiomorpholino |
| 187 | 2 | 3,4-(OEt)₂Ph | Me | H | H | thiomorpholino |
| 188 | 2 | 3,4-CH₂(O₂)Ph | Me | H | H | thiomorpholino |
| 189 | 2 | t-octyl | Me | H | H | thiomorpholino |
| 190 | 2 | 2-thienyl | Me | H | H | thiomorpholino |
| 191 | 2 | 2-furyl | Me | H | H | thiomorpholino |
| 192 | 2 | 6-Cl-3-Pyridyl | Me | H | H | thiomorpholino |
| 193 | 2 | 6-OMe-3-Pyridyl | Me | H | H | thiomorpholino |
| 194 | 2 | 6-Me-3-Pyridyl | Me | H | H | thiomorpholino |
| 195 | 2 | 2,6-(Me)₂-3-Pyridyl | Me | H | H | thiomorpholino |
| 196 | 2 | t-butyl | Me | H | H | thiomorpholino |

-continued
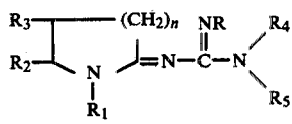
| Compound No. | n | R | $R_1$ | $R_2$ | $R_3$ | $-NR_4R_5$ |
|---|---|---|---|---|---|---|
| 197 | 2 | t-octyl | Me | H | H | -N⌒S (thiomorpholino) |
| 198 | 2 | 9-fluorenyl | Me | H | H | -N⌒S |
| 199 | 2 | $CH(Ph)_2$ | Me | H | H | -N⌒S |
| 200 | 2 | cyclohexyl | Me | H | H | -N⌒S |
| 201 | 2 | 2-adamantyl | Me | H | H | -N⌒S |
| 202 | 2 | α,α-$(Me)_2$Benzyl | Me | H | H | -N⌒S |
| 203 | 2 | α,α-$(CH_2)_4CCH_2Ph$ | Me | H | H | -N⌒S |
| 204 | 2 | 1-tetralinyl | Me | H | H | -N⌒S |
| 205 | 2 | exo-2-norbornyl | Me | H | H | -N⌒S |
| 206 | 1 | 4-SMePh | $CH_2CH_2OH$ | H | H | -N⌒S |
| 207 | 1 | 3-ClPh | $CH_2CH_2OH$ | H | H | -N⌒S |
| 208 | 1 | 4-FPh | Me | Me | H | -N⌒S |
| 209 | 1 | 3-$CF_3$Ph | Et | H | H | -N⌒S |
| 210 | 1 | 4-OC(O)MePh | allyl | H | H | -N⌒S |

-continued
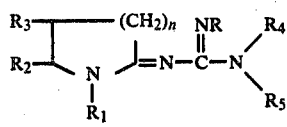
| Compound No. | n | R | R₁ | R₂ | R₃ | —NR₄R₅ |
|---|---|---|---|---|---|---|
| 211 | 1 | 2-naphthyl | CH₂CH₂OH | H | H | —N⏜S |
| 212 | 1 | 3-OEt-4-OMePh | ◯ | H | H | —N⏜S |
| 213 | 1 | 3,4-CH₂(O₂)Ph | allyl | H | H | —N⏜S |
| 214 | 1 | neopentyl | Me | H | Me | —N⏜S |
| 215 | 1 | t-octyl | Me | H | H | —N⏜S |
| 216 | 1 | 2-thienyl | Me | H | H | —N⏜S |
| 217 | 1 | 2-furyl | Me | H | H | —N⏜S |
| 218 | 1 | 6-Cl-3-Pyridyl | Me | H | H | —N⏜S |
| 219 | 1 | 6-OMe-3-Pyridyl | allyl | H | H | —N⏜S |
| 220 | 1 | 6-Me-3-Pyridyl | Et | H | H | —N⏜S |
| 221 | 1 | 2,6-(Me)₂-3-Pyridyl | Me | Me | H | —N⏜S |
| 222 | 1 | 2,6-(OMe)₂-3-Pyridyl | Me | n-Bu | H | —N⏜S |
| 223 | 1 | 9-fluorenyl | Me | H | H | —N⏜S |
| 224 | 1 | CH(Ph)₂ | Me | H | H | —N⏜S |

-continued
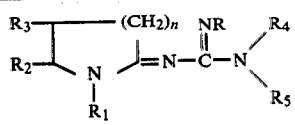
| Compound No. | n | R | $R_1$ | $R_2$ | $R_3$ | $-NR_4R_5$ |
|---|---|---|---|---|---|---|
| 225 | 1 | 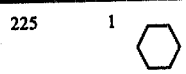 | Me | H | H | 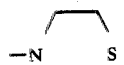 |
| 226 | 1 | 3,5(Me)$_2$Ph | Me | H | H |  |
| 227 | 1 | 3,4-Cl$_2$Ph | Me | H | H | 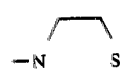 |
| 228 | 1 | 3-BrPh | Me | H | H | 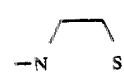 |
| 229 | 1 | 1-adamantyl | Me | H | H | 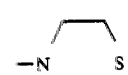 |
| 230 | 1 | exo-2-norbornyl | Me | H | H |  |
| 231 | 1 | 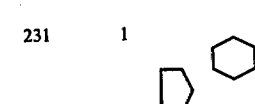 | Me | H | H | 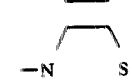 |
| 232 | 1 | 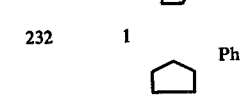 | Me | H | H | 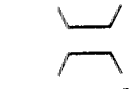 |
| 233 | 1 | anti-7-norbornenyl | Me | H | H | 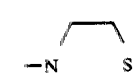 |
| 234 | 1 | α,α-(CH$_2$)$_4$CCH$_2$Ph | Me | H | H | 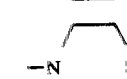 |
| 235 | 1 | α,α-(Me)$_2$Benzyl | Me | H | H | 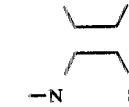 |
| 236 | 1 | 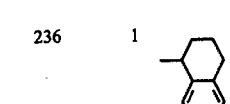 | Me | H | H | 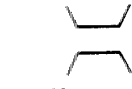 |
| 237 | 1 | 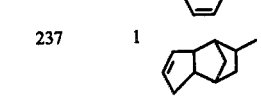 | Me | H | H | 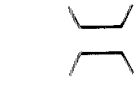 |
| 238 | 1 | 4-OC(O)CH(CH$_3$)$_2$Ph | Me | H | H | 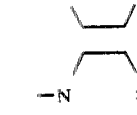 |

-continued

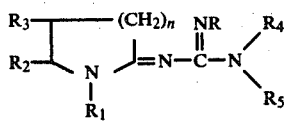

| Compound No. | n | R | $R_1$ | $R_2$ | $R_3$ | —$NR_4R_5$ |
|---|---|---|---|---|---|---|
| 239 | 1 | —C(CH$_3$)$_2$CH$_2$Ph | Me | H | H | —N(thiomorpholine) |
| 240 | 1 | 3-EtPh | —CH$_2$CH$_2$OH | H | H | —N(thiomorpholine) |
| 241 | 3 | 3-OMePh | Me | H | H | —N(hexamethyleneimine) |
| 242 | 3 | 4-SMePh | Me | H | H | —N(hexamethyleneimine) |
| 243 | 3 | 3,4-(OMe)$_2$Ph | Me | H | H | —N(hexamethyleneimine) |
| 244 | 3 | 3-ClPh | Me | H | H | —N(hexamethyleneimine) |
| 245 | 3 | 4-FPh | Me | H | H | —N(hexamethyleneimine) |
| 246 | 3 | 3-MePh | Me | H | H | —N(hexamethyleneimine) |
| 247 | 3 | 3,4-CH$_2$O$_2$Ph | Me | H | H | —N(hexamethyleneimine) |
| 248 | 2 | 4-OEtPh | Me | H | H | —N(hexamethyleneimine) |
| 249 | 2 | 4-SMePh | Me | H | H | —N(hexamethyleneimine) |
| 250 | 2 | 3,4-(OMe)$_2$Ph | Me | H | H | —N(hexamethyleneimine) |
| 251 | 2 | 3,5-Cl$_2$Ph | Me | H | H | —N(hexamethyleneimine) |
| 252 | 2 | 2,4-(Me)$_2$Ph | Me | H | H | —N(hexamethyleneimine) |

-continued

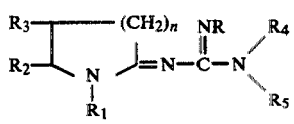

| Compound No. | n | R | $R_1$ | $R_2$ | $R_3$ | $-NR_4R_5$ |
|---|---|---|---|---|---|---|
| 253 | 2 | 4-OC(O)MePh | Me | H | H | hexamethyleneimino |
| 254 | 2 | 4-N(Me)EtPh | Me | H | H | hexamethyleneimino |
| 255 | 2 | 4-S(O)MePh | Me | H | H | hexamethyleneimino |
| 256 | 1 | cyclohexyl | Me | H | H | hexamethyleneimino |
| 257 | 1 | 9-fluorenyl | Me | H | H | hexamethyleneimino |
| 258 | 1 | 2-norbornyl | Me | H | H | hexamethyleneimino |
| 259 | 1 | 1-adamantyl | Me | H | H | hexamethyleneimino |
| 260 | 1 | 2-naphthyl | Me | H | H | hexamethyleneimino |
| 261 | 1 | α,α-(Me)$_2$Benzyl | Me | H | H | hexamethyleneimino |
| 262 | 1 | benzyl | Me | H | H | hexamethyleneimino |
| 263 | 1 | Ph | CH$_2$CH$_2$OH | H | H | hexamethyleneimino |
| 264 | 1 | Ph | allyl | H | H | hexamethyleneimino |
| 265 | 1 | Ph | Me | Me | H | hexamethyleneimino |
| 266 | 1 | 4-OC(O)MePh | Et | H | H | hexamethyleneimino |

-continued
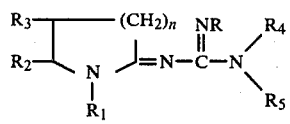
| Compound No. | n | R | $R_1$ | $R_2$ | $R_3$ | $-NR_4R_5$ |
|---|---|---|---|---|---|---|
| 267 | 1 | 4-FPh | Me | H | Me | -N(azepane) |
| 268 | 1 | 3-BrPh | Me | H | H | -N(azepane) |
| 269 | 1 | 3-OMePh | Et | H | H | -N(azepane) |
| 270 | 1 | 4-MePh | Me | H | H | -N(azepane) |
| 271 | 1 | 4-SMePh | $-CH_2CH_2OH$ | H | H | -N(azepane) |
| 272 | 1 | 3,4-$(OMe)_2$Ph | Et | H | H | -N(azepane) |
| 273 | 1 | 3,4-$CH_2O_2$Ph | Me | n-Bu | H | -N(azepane) |
| 274 | 1 | 3,5-$Cl_2$Ph | Me | H | Me | -N(azepane) |
| 275 | 1 | Ph | Me | H | H | -N(azepane) |
| 276 | 1 | 4-$N(Me)_2$Ph | Me | Me | H | -N(azepane) |
| 277 | 1 | $-CH(Ph)_2$ | Me | H | H | -N(azepane) |
| 278 | 1 | 4-$OCH_2$PhPh | Me | H | H | -N(azepane) |
| 279 | 3 | 3-ClPh | Me | H | H | -N(N-Me piperazine) |
| 280 | 3 | 3-MePh | Me | H | H | -N(N-Me piperazine) |

-continued

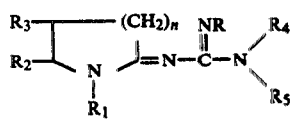

| Compound No. | n | R | R₁ | R₂ | R₃ | —NR₄R₅ |
|---|---|---|---|---|---|---|
| 281 | 3 | 4-SMePh | Me | H | H | —N(piperazine)N—Me |
| 282 | 3 | 3-CF₃Ph | Me | H | H | —N(piperazine)N—Me |
| 283 | 3 | t-octyl | Me | H | H | —N(piperazine)N—Me |
| 284 | 3 | 4-FPh | Me | H | H | —N(piperazine)N—Me |
| 285 | 3 | 3,4-(OMe)₂Ph | Me | H | H | —N(piperazine)N—Me |
| 286 | 2 | 4-ClPh | Me | H | H | —N(piperazine)N—Me |
| 287 | 2 | 4-MePh | Me | H | H | —N(piperazine)N—Me |
| 288 | 2 | 3,4-CH₂(O,O)Ph | Me | H | H | —N(piperazine)N—Me |
| 289 | 3 | 4-FPh | Me | H | H | —N(piperazine)N—Ph |
| 290 | 2 | 3-OMePh | Me | H | H | —N(piperazine)N—Ph |
| 291 | 1 | 4-MePh | Me | H | H | —N(piperazine)N—Ph |
| 292 | 1 | 3,4-CH₂(O,O)Ph | allyl | H | H | —N(piperazine)N—Ph |
| 293 | 1 | 4-SMePh | Et | H | H | —N(piperazine)N—Ph |
| 294 | 1 | t-butyl | Me | Me | H | —N(piperazine)N—Ph |

-continued

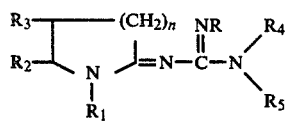

| Compound No. | n | R | R₁ | R₂ | R₃ | —NR₄R₅ |
|---|---|---|---|---|---|---|
| 295 | 1 | cyclohexyl | CH₂CH₂OH | H | H | —N(piperazinyl)N—Ph |
| 296 | 1 | 3,4-(OMe)₂Ph | Me | n-Bu | H | —N(piperazinyl)N—Ph |
| 297 | 3 | 3-OMe PH | Me | H | H | —N(piperazinyl)N—CH₂Ph |
| 298 | 3 | 3,4-CH₂(O,O)Ph | Me | H | H | —N(piperazinyl)N—CH₂Ph |
| 299 | 3 | 3-MePh | Me | H | H | —N(piperazinyl)N—CH₂Ph |
| 300 | 2 | 3-ClPh | Me | H | H | —N(piperazinyl)N—CH₂Ph |
| 301 | 2 | 3-CF₃Ph | Me | H | H | —N(piperazinyl)N—CH₂Ph |
| 302 | 2 | neopentyl | Me | H | H | —N(piperazinyl)N—CH₂Ph |
| 303 | 2 | 3,4-(OEt)₂Ph | Me | H | H | —N(piperazinyl)N—CH₂Ph |
| 304 | 2 | 3-MePh | Me | H | H | —N(piperazinyl)N—CH₂Ph |
| 305 | 2 | 3,4-CH₂(O,O)Ph | Me | H | H | —N(piperazinyl)N—CH₂Ph |
| 306 | 1 | 4-OEtPh | Me | Me | H | —N(piperazinyl)N—CH₂Ph |
| 307 | 1 | 3-BrPh | allyl | H | H | —N(piperazinyl)N—CH₂Ph |
| 308 | 1 | 4-MePh | CH₂CH₂OH | H | H | —N(piperazinyl)N—CH₂Ph |

-continued

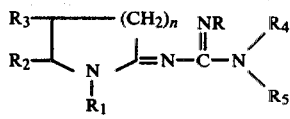

| Compound No. | n | R | R₁ | R₂ | R₃ | —NR₄R₅ |
|---|---|---|---|---|---|---|
| 309 | 1 | 4-OC(O)MePh | Me | H | Me | —N⟨N—CH₂Ph⟩ (piperazine) |
| 310 | 1 | 4-SMePh | Me | n-Bu | H | —N⟨N—CH₂Ph⟩ (piperazine) |
| 311 | 1 | t-octyl | Me | H | H | N⟨NH⟩ with Me, Me (dimethylpiperazine) |
| 312 | 2 | 3,5-Cl₂Ph | Me | H | H | " |
| 313 | 2 | 3,CF₃Ph | Me | H | H | " |
| 314 | 3 | 3-OMePh | Me | H | H | " |
| 315 | 1 | 3,4-(Me)₂Ph | Me | Me | H | " |

What is claimed is:

1. A chemical compound selected from the group consisting of a guanidine derivative having the formula:

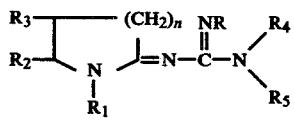

and the pharmaceutically acceptable acid addition and quaternary salts thereof, wherein:

n is the integer 1, 2 or 3;

R₁ is a member selected from the group consisting of hydrogen, alkyl having from 1 to 8 carbons, cycloalkyl having from 3 to 6 carbons, alken-2-yl having from 3 to 5 carbons, hydroxyloweralkyl, benzyl and phenyl;

R₂ is a member selected from the group consisting of hydrogen, alkyl having from 1 to 6 carbons and phenyl;

R₃ is a member selected from the group consisting of hydrogen, alkyl having from 1 to 8 carbons and phenyl;

R₄ is a member selected from the group consisting of hydrogen, methyl and ethyl;

R₅ is a member selected from the group consisting of alkyl having from 1 to 4 carbons, cycloalkyl having from 3 to 7 carbons, benzyl, and phenyl and phenyl substituted with from 1 to 3 substituents each selected from the group consisting of halo, loweralkyl and loweralkoxy;

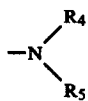

taken together represents a 3- to 7-membered saturated azacarbocyclic ring; provided that when -NR₄R₅ represents a six-membered ring, (i) said ring may, if desired, be interrupted by an oxygen or sulfur atom or by an additional nitrogen atom, which additional nitrogen atom may be substituted with loweralkyl, phenyl, or benzyl, or (ii) said ring may be substituted with loweralkyl, at a carbon atom other than one immediately adjacent the nitrogen atom which is bonded to the carboximidamide function, selected from the group consisting of aziridinyl, azetidinyl, pyrrolidinyl, piperidino, 2,3,4,5,6,7-hexahydroazepinyl, morpholino, thiamorpholino, thiamorpholino-1-oxide, thiamorpholino-1, 1-dioxide, 2, 6-diloweralkyl-morpholino 4-loweralkyl-piperazinyl, 4-phenyl-piperazinyl, 4-

R is a member selected from the group consisting of:
alkyl having from 4 to 10 carbons;
cycloalkyl having from 5 to 8 carbons;
bicycloalkyl having from 7 to 10 carbons;
bicycloalkenyl having from 7 to 10 carbons;
tricycloalkyl having from 9 to 10 carbons;
1-adamantylmethyl;
tricycloalkenyl having from 9 to 10 carbons;
arylalkyl in which the aryl function is a member selected from the group consisting of phenyl and naphthyl and the alkyl function has from 1 to 4 carbons;
α,A-tetramethylene-phenethyl;
diphenylalkyl in which the alkyl function has from 1 to 2 carbons;
naphthyl;
fused diarylcycloalkenyl;
fused arylcycloalkyl;
phenylcycloalkyl in which the cycloalkyl function has from 5 to 7 carbons;
cycloalkylcycloalkyl in which each cycloalkyl function has from 5 to 7 carbons;
phenyl; methylenedioxyphenyl; phenyl substituted with from 1 to 3 substituents each selected from the group consisting of halo, loweralkyl and loweralkoxy; and phenyl substituted with a member selected from the group consisting of amino, dimethylamino, methylethylamino, diethylamino, loweralkanoylamino, thioloweralkyl, sulfinylloweralkyl, sulfonylloweralkyl, trifluoromethyl, hydroxy, benzyloxy, loweralkanoyloxy, loweralkanoyl and nitro; and 3-Pyridyl, and said 3-pyridyl substituted at the ring carbons with 1 to 2 members selected from the group consisting of halo, loweralkyl, and loweralkoxy.

2. A chemical compound selected from the group consisting of a guanidine derivative having the formula:

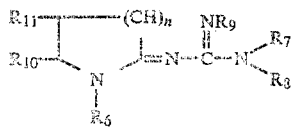

and the pharmaceutically acceptable acid addition and quaternary salts thereof wherein:

$n = 1$ or 2;

$R_6$ is a member selected from the group consisting of loweralkyl, allyl, hydroxy-loweralkyl and benzyl;

$R_7$ is a member selected from the group consisting of methyl and ethyl;

$R_8$ is a member selected from the group consisting of loweralkyl, cyclopentyl and cyclohexyl;

—$NR_7R_8$ taken together is a member selected from the group consisting of pyrrolidino, piperidino, morpholino and thiomorpholino;

$R_9$ is a member selected from the group consisting of 1-adamantyl, 1,1,3,3-tetramethyl-butylphenyl; methylenedioxyphenyl, phenyl substituted with from 1 to 3 substituents each selected from the group consisting of halo, loweralkyl and loweralkoxy; and phenyl substituted with a member selected from the group consisting of amino, dimethylamino, methylethylamino, diethylamino, loweralkanoylamino, thioloweralkyl, sulfinylloweralkyl, trifluoromethyl, hydroxy, benzyloxy, loweralkanoyloxy, loweralkanoyl and nitro;

$R_{10}$ is a member selected from the group consisting of hydrogen and alkyl of 1 to 3 carbons; and $R_{11}$ is a member selected from the group consisting of hydrogen and alkyl of 1 to 3 carbons; provided that at least one of said $R_{10}$ and $R_{11}$ is hydrogen.

3. A compound of claim 1 selected from the group consisting of N-(1-methyl-2-pyrrolidinylidene)-N'-phenyl-1-pyrrolidinecarboximidamide and the pharmaceutically acceptable acid addition and quaternary salts thereof.

4. A compound of claim 1 selected from the group consisting of N-(1-methyl-2-pyrrolidinylidene)-N'-phenyl-4-morpholinecarboximidamide and the pharmaceutically acceptable acid addition and quaternary salts thereof.

5. A compound of claim 1 selected from the group consisting of N-(1-methyl-2-pyrrolidinylidene)-N'-p-methoxyphenyl-1-pyrrolidinecarboximidamide and the pharmaceutically acceptable acid addition and quaternary salts thereof.

6. A compound of claim 1 selected from the group consisting of N-(1-methyl-2-piperidinylidene-N'-phenyl-1-pyrrolidinecarboximidamide and the pharmaceutically acceptable acid addition and quaternary salts thereof.

7. A compound of claim 1 selected from the group consisting of N-(1-methyl-2-pyrrolidinylidene)-N'-(1,1,3,3-tetramethylbutyl)-1-pyrrolidinecarboximidamide and the pharmaceutically acceptable acid addition and quaternary salts thereof.

8. A compound of claim 1 selected from the group consisting of N-(1-allyl-2-pyrrolidinylidene)-N'-phenyl-1-piperidinecarboximidamide and the pharmaceutically acceptable acid addition and quaternary salts thereof.

9. A compound of claim 1 selected from the group consisting of N-(1-methyl-2-pyrrolidinylidene)-N'-cyclopentyl-N'-methyl-N''-phenylguanidine and the pharmaceutically acceptable acid addition and quaternary salts thereof.

10. A compound of claim 1 selected from the group consisting of N-(1-methyl-2-pyrrolidinylidene)-N'-phenyl-4-thiamorpholinecarboximidamide and the pharmaceutically acceptable acid addition and quaternary salts thereof.

11. A compound of claim 1 selected from the group consisting of N-(1-Methyl-2-pyrrolidinylidene)-N'-phenyl-1-piperidinecarboximidamide and the pharmaceutically acceptable acid addition and quaternary salts thereof.

12. A compound of claim 1 selected from the group consisting of N-(4-Fluorophenyl)-N'-(1-methyl-2-pyrrolidinylidene)-1-pyrrolidinecarboximidamide and the pharmaceutically acceptable acid addition and quaternary salts thereof.

13. A compound of claim 1 selected from the group consisting of N-(4-Methylphenyl)-N'-(1-methyl-2-pyrrolidinylidene)-1-pyrrolidinecarboximidamide and the pharmaceutically acceptable acid addition and quaternary salts thereof.

14. A compound of claim 1 from the group consisting of N-(1-Methyl-2-pyrrolidinylidene)-N'-(3,4-methylenedioxyphenyl)-1-piperidinecarboximidamide and the pharmaceutically acceptable acid addition and quaternary salts thereof.

15. A compound of claim 1 selected from the group consisting of N-(3-Chlorophenyl)-N'-(1-methyl-2-pyrrolidinylidene)-4-morpholinecarboximidamide and the pharmaceutically acceptable acid addition and quaternary salts thereof.

16. A compound of claim 1 selected from the group consisting of N-Cyclopentyl-N-methyl-N'-(3-methylphenyl)-N''-(1-methyl-2-pyrrolidinylidene)guanidine and the pharmaceutically acceptable acid addition and quaternary salts thereof.

17. A compound of claim 1 selected from the group consisting of N-Cyclohexyl-N'-(4-methoxyphenyl)-N-methyl-N''-(1-methyl-2-pyrrolidinylidene)guanidine and the pharmaceutically acceptable acid addition and quaternary salts thereof.

18. A compound of claim 1 selected from the group consisting of N-(4-Acetyloxyphenyl)-N'-(1-methyl-2-pyrrolidinylidene)-1-pyrrolidinecarboximidamide and the pharmaceutically acceptable acid addition and quaternary salts thereof.

19. A compound of claim 1 selected from the group consisting of N-(4-Methylphenyl)-N'-(1-methyl-2-pyrrolidinylidene)-4-morpholinecarboximidamide and the pharmaceutically acceptable acid addition and quaternary salts thereof.

20. A compound of claim 1 selected from the group consisting of N-(4-Methylphenyl)-N'-(1-methyl-2-pyrrolidinylidene)-4-thiomorpholinecarboximidamide and the pharmaceutically acceptable acid addition and quaternary salts thereof.

21. A compound of claim 1 selected from the group consisting of N-(3-Methylphenyl)-N'-(1-methyl-2-piperidinylidene)-4-morpholinecarboximidamide and the pharmaceutically acceptable acid addition and quaternary salts thereof.

22. A compound of claim 1 selected from the group consisting of N-(3-Methylphenyl)-N'-(1-methyl-2-pyrrolidinylidene)-4-morpholinecarboximidamide and the pharmaceutically acceptable acid addition and quaternary salts thereof.

23. A compound of claim 1 selected from the group consisting of N-(4-Chlorophenyl)-N'-(1-methyl-2-pyrrolidinylidene)-1-pyrrolidinecarboximidamide and the pharmaceutically acceptable acid addition and quaternary salts thereof.

24. A compound of claim 1 selected from the group consisting of 4-Methyl-N-(1-methyl-2-pyrrolidinylidene)-N'-phenyl-1-piperazinecarboximidamide and the pharmaceutically acceptable acid addition and quaternary salts thereof.

25. A compound of claim 1 selected from the group consisting of N-(1-Adamantyl)-N'-(1-methyl-2-pyrrolidinylidene)-1-pyrrolidinecarboximidamide and the pharmaceutically acceptable acid addition and quaternary salts thereof.

26. A compound of claim 1 selected from the group consisting of N-(1-methyl-2-pyrrolidinylidene)-N'-(2-naphthyl)-1-pyrrolidinecarboximidamide and the pharmaceutically acceptable acid addition and quaternary salts thereof.

27. A compound of claim 1 selected from the group consisting of 4-Phenyl-N-(1-methyl-2-pyrrolidinylidene)-N'-phenyl-1-piperazinecarboximidamide and the pharmaceutically acceptable acid addition and quaternary salts thereof.

28. A compound of claim 1 selected from the group consisting of N-Cyclohexyl-N'-(1-methyl-2-pyrrolidinylidene)-1-pyrrolidinecarboximidamide and the pharmaceutically acceptable acid addition and quaternary salts thereof.

29. A compound of claim 1 selected from the group consisting of N-(1-Methyl-2,3,4,5,6,7-hexahydroazepinylidene)-N'-phenyl-1-pyrrolidinecarboximidamide and the pharmaceutically acceptable acid addition and quaternary salts thereof.

30. A compound of claim 1 selected from the group consisting of N-(1-Ethyl-2-pyrrolidinylidene)-N'-phenyl-1-pyrrolidinecarboximidamide and the pharmaceutically acceptable acid addition and quaternary salts thereof.

31. A compound of claim 1 selected from the group consisting of N-(Diphenylmethyl)-N'-(1-methyl-2-pyrrolidinylidene)-1-pyrrolidinecarboximidamide and the pharmaceutically acceptable acid addition and quaternary salts thereof.

32. A compound of claim 1 selected from the group consisting of N-Cyclohexyl-N-methyl-N'-(1-methyl-2-pyrrolidinylidene)-N''-(1-naphthyl)guanidine and the pharmaceutically acceptable acid addition and quaternary salts thereof.

33. A compound of claim 1 selected from the group consisting of N-(1,5-Dimethyl-2-pyrrolidinylidene)-N'-phenyl-1-pyrrolidinecarboximidamide and the pharmaceutically acceptable acid addition and quaternary salts thereof.

34. A compound of claim 1 selected from the group consisting of N,N-Diethyl-N'-(1-methyl-2-pyrrolidinylidene)-N''-phenylguanidine and the pharmaceutically acceptable acid addition and quaternary salts thereof.

35. A compound of claim 1 selected from the group consisting of N-(1-Ethyl-2-pyrrolidinylidene)-N'-(4-methoxyphenyl)-1-pyrrolidinecarboximidamide and the pharmaceutically acceptable acid addition and quaternary salts thereof.

36. N-(2,6-Dichlorophenyl)-N'-(1-methyl-2-pyrrolidinylidene)-1-pyrrolidinecarboximidamidinuim Methofluorosulfonate.

37. A compound of claim 1 selected from the group consisting of N-(1-Benzyl-2-pyrrolidinylidene)-N'-phenyl-4-morpholinecarboximidamide and the pharmaceutically acceptable acid addition and quaternary salts thereof.

38. A compound of claim 1 selected from the group consisting of N-[1-(2-Hydroxyethyl)-2-pyrrolidinylidene]-N'-phenyl-4-morpholinecarboximidamide and the pharmaceutically acceptable acid addition and quaternary salts thereof.

39. A compound of claim 1 selected from the group consisting of N-(9H-Fluoren-9-yl)N'-(1-methyl-2-pyrrolidinylidene)-1-pyrrolidinecarboximidamide and the pharmaceutically acceptable acid addition and quaternary salts thereof.

40. A compound of claim 1 selected from the group consisting of N-Diphenylmethyl-N'-(1-methyl-2-piperidinylidene)-4-morpholinecarboximidamide and the pharmaceutically acceptable acid addition and quaternary salts thereof.

41. A compound of claim 1 selected from the group consisting of N-(3-Methoxyphenyl)-N'-(1-methyl-2-pyrrolidinylidene)-1-piperidinecarboximidamide and the pharmaceutically acceptable acid addition and quaternary salts thereof.

42. A compound of claim 1 selected from the group consisting of N-(3,4-Dimethoxyphenyl)-N'-(1-methyl-2-pyrrolidinylidene)-1-pyrrolidinecarboximidamide and the pharmaceutically acceptable acid addition and quaternary salts thereof.

43. A compound of claim 1 selected from the group consisting of N-(1-Methyl-2-pyrrolidinylidene)-N'-(4-methylthiophenyl)-4-morpholinecarboximidamide and the pharmaceutically acceptable acid addition and quaternary salts thereof.

44. A compound of claim 1 selected from the group consisting of N-(1-Methyl-2-pyrrolidinylidene)-N'-phenyl-4-(2,6-dimethyl) morpholinecarboximidamide and the pharmaceutically acceptable acid addition and quaternary salts thereof.

45. A compound of claim 1 selected from the group consisting of N-(4-Benzyloxyphenyl)-N'-(1-methyl-2-pyrrolidinylidene)-1-pyrrolidinecarboximidamide and the pharmaceutically acceptable acid addition and quaternary salts thereof.

46. A compound of claim 1 selected from the group consisting of N-(1-Allyl-2-pyrrolidinylidene)-N'-(3-methylphenyl)-4-thiomorpholinecarboximidamide and the pharmaceutically acceptable acid addition and quaternary salts thereof.

47. A compound of claim 1 selected from the group consisting of N-(3-Methoxyphenyl)-N'-(1-methyl-2-pyrrolidinylidene)-4-thiomorpholinecarboximidamide and the pharmaceutically acceptable acid addition and quaternary salts thereof.

48. A compound of claim 2, which is N-(4-hydroxyphenyl)-N'-(1-methyl-2-pyrrolidinylidene)-1-pyrrolidinecarboximidamide hydroiodide.

* * * * *